United States Patent
Wang et al.

(10) Patent No.: US 12,391,946 B2
(45) Date of Patent: Aug. 19, 2025

(54) USE OF A JANUS KINASE INHIBITOR AND A TELOMERASE INHIBITOR FOR THE TREATMENT OF MYELOPROLIFERATIVE NEOPLASMS

(71) Applicants: Geron Corporation, Foster City, CA (US); Icahn School of Medicine at Mount Sinai, New York, NY (US)

(72) Inventors: Xiaoli Wang, New York, NY (US); Fei Huang, Foster City, CA (US)

(73) Assignee: Geron Corporation, Foster City, CA (US)

( * ) Notice: Subject to any disclaimer, the term of this patent is extended or adjusted under 35 U.S.C. 154(b) by 441 days.

(21) Appl. No.: 17/088,303

(22) Filed: Nov. 3, 2020

(65) Prior Publication Data

US 2021/0269807 A1 Sep. 2, 2021

Related U.S. Application Data

(60) Provisional application No. 62/930,251, filed on Nov. 4, 2019.

(51) Int. Cl.
| | | |
|---|---|---|
| *C12N 15/11* | (2006.01) | |
| *A61K 31/506* | (2006.01) | |
| *A61K 31/519* | (2006.01) | |
| *A61K 31/529* | (2006.01) | |
| *A61K 31/5377* | (2006.01) | |
| *C12N 15/113* | (2010.01) | |

(52) U.S. Cl.
CPC ........ *C12N 15/1137* (2013.01); *A61K 31/506* (2013.01); *A61K 31/519* (2013.01); *A61K 31/529* (2013.01); *A61K 31/5377* (2013.01); *C12N 2310/315* (2013.01); *C12N 2310/3515* (2013.01)

(58) Field of Classification Search
CPC .... A61P 35/00; C12N 2310/11; C12N 15/113
See application file for complete search history.

(56) References Cited

U.S. PATENT DOCUMENTS

| | | | | |
|---|---|---|---|---|
| 2014/0135350 A1* | 5/2014 | Ni | ........................... | A61P 35/00 514/265.1 |
| 2015/0342982 A1* | 12/2015 | Stuart | ................ | A61K 31/7125 514/44 A |

FOREIGN PATENT DOCUMENTS

| | | |
|---|---|---|
| WO | WO2013067043 | 5/2013 |
| WO | WO2014088785 | 12/2014 |

OTHER PUBLICATIONS

Harrison et al., Current treatment algorithm for the management of patients with myelofibrosis, JAK inhibitors, and beyond, Hematology, pp. 489-497. (Year: 2017).*

Doherty et al., Life, death and autophagy, Nature Cell Biology, vol. 20, pp. 1110-1117. (Year: 2018).*
Sergei M. Gryaznov, Oligonucleotide N3' → P5' phosphoramidates and thio-phosphoramidates as potential therapeutic agents, Chemistry & Biodiversity, vol. 7, pp. 477-493. (Year: 2010).*
Jackson et al., Antiadhesive effects of GRN163L—an oligonucleotide N3' → P5' thio-phosphoramidate targeting telomerase, Cancer Research, vol. 67, pp. 1121-1129. (Year: 2007).*
Østergaard et al., Conjugation of hydrophobic moieties enhances potency of antisense oligonucleotides in the muscle of rodents and non-human primates, Nucleic Acids Research, vol. 47, pp. 6045-6058. (Year: 2019).*
Prakash et al., Fatty acid conjugation enhances potency of antisense oligonucleotides in muscle, Nucleic Acids Research, vol. 47, pp. 6029-6044. (Year: 2019).*
Caocci et al., Ruxolitinib restores normal telomere length in patients with myelofibrosis, Blood, vol. 128, issue 22, p. 3116, abstract No. 634. (Year: 2016).*
Hao et al., (2019) "Cotargeting the JAK/STAT signaling pathway and histone deacetylase by ruxolitinib and vorinostat elicits synergistic effects against myeloproliferative neoplasms", Investigational New Drugs, vol. 38, pp. 610-620.
Hu et al., (2019) "Combination Treatment with Imetelstat, a Telomerase Inhibitor, and Ruxolitinib Depletes Myelofibrosis Hematopoietic Stem Cells and Progenitor Cells", Blood, vol. 134, Suppl. 1, p. 1 of 1.
Rampal et al., (2018) "Safety and efficacy of combined ruxolitinib and decitabine in accelerated and blast-phase myeloproliferative neoplasms", Blood Advances, vol. 2, No. 24, pp. 3572-3580.
Tefferi et al. (2015) "A pilot study of the telomerase inhibitor imetelstat for myelofibrosis," N. Engl. J. Med., vol. 373, No. 10, pp. 908-919.
Wang et al., (2018) "Imetelstat, a telomerase inhibitor, is capable of depleting myelofibrosis stem and progenitor cells", Blood Advances, vol. 2, No. 18, pp. 2378-2388.
Baerlocher et al., (2012) "Imetelstat rapidly Induces and Maintains Substantial Hematologic and Molecular Responses in Patients with Essential Thrombocythemia (ET) who are Refractory or Intolerant to Prior Therapy: Preliminary Phase II Results", Blood (ASH Meeting Abstracts), vol. 120, No. 21, Abstract 179, pp. 1-16.
Barosi et al., (2004) "Spleen neoangiogenesis in patients with myelofibrosis with myeloid metaplasia. British Journal Haematol", vol. 124, pp. 618-625. Erratum in: Br J Haematol. 2004; 126: 284-5.
Brennan et al., (2010) "Telomerase inhibition targets clonogenic multiple myeloma cells through telomere length-dependent and independent mechanisms", PLoS One, vol. 5, Issue 9, e12487, pp. 1-8.

(Continued)

*Primary Examiner* — Dana H Shin
(74) *Attorney, Agent, or Firm* — Rudy J. Ng; Travis Young; Bozicevic, Field & Francis LLP

(57) ABSTRACT

Aspects of the disclosure include methods for treating a myeloproliferative neoplasm. Methods according to certain embodiments include co-administering to a subject a Janus kinase (JAK) inhibitor and a telomerase inhibitor comprising an oligonucleotide and a lipid moiety linked to the 5' and/or 3' end of the oligonucleotide. Methods for inducing apoptosis of a myeloproliferative neoplasm cell by contacting the cell with an amount of a JAK inhibitor and a telomerase inhibitor sufficient to induce apoptosis are also described. Compositions having a JAK inhibitor and a telomerase inhibitor for practicing the subject methods are also provided.

15 Claims, 16 Drawing Sheets

Specification includes a Sequence Listing.

(56) References Cited

OTHER PUBLICATIONS

Brunold et al., (2011) "Imetelstat, A Potent Telomerase Inhibitor, Inhibits the Spontaneous Growth of CFU-Meg In Vitro From Essential Thrombocythemia Patients but Not From Healthy Individuals", Blood (ASH Annual Meeting Abstracts), vol. 118, No. 21, Abstract 3843, pp. 1-3.
Greider and Blackburn, (1985) "Identification of a specific telomere terminal transferase activity in Tetrahymena extracts", Cell, vol. 43, pp. 405-413.
Hoffmanand BenzJr E, Silberstein L, Heslop H, Weitz J and Anastasi J. Chapter 53—Progress in the Classification of Myeloid Neoplasms: Clinical Implications In: Hoffman R, et al. Hematology: Basic Principles and Practice, 6th ed. New York, New York, USA:Saunders, An Imprint of Elsevier; 2012:722-727.
Joseph et al., (2010) "The telomerase inhibitor Imetelstat depletes cancer stem cells in breast and pancreatic cancer cell lines", Cancer Research., vol. 70, pp. 9494-9504.
Kim et al., (1994) "Specific association of human telomerase activity with immortal cells and cancer", Science, vol. 266, pp. 2011-2015.
Kralovics and Skoda, (2005) "Molecular pathogenesis of Philadelphia chromosome negative myeloproliferative disorders", Blood Reviews, vol. 19, No. 1, pp. 1-13.
Marian et al., (2010) "The effects of telomerase inhibition on prostate tumor-initiating cells", International Journal of Cancer, vol. 127, 321-331.
Marian et al., (2010) "The telomerase antagonist, Imetelstat, efficiently targets glioblastoma tumor-initiating cells leading to decreased proliferation and tumor Growth", Clinical Cancer Research., 16: 154-163.
Mesa, Ruben A., (2002) "Clinical and scientific advances in the Philadelphia-chromosome negative chronic myeloproliferative disorders", Int J Hematol., vol. 76, Sup. II, pp. 193-203.
Nussenzveig et al., (2007) "Polycythemia vera is not initiated by $JAK2^{V617F}$ mutation", Experimental Hematology, vol. 35, No. 1, pp. 32-38.
Prchal JF, and Prchal JT., (1999) "Molecular basis for polycythemia", Current Opinion Hematology, vol. 6, No. 2, pp. 100-109.
Shay and Bacchetti, (1997) "A survey of telomerase activity in human cancer", European Journal of Cancer, vol. 33, No. 5, pp. 787-791.
Shay and Wright, (1996) "Telomerase activity in human cancer", Curr Opin Oncol., vol. 8, pp. 66-71.
Shea-Herbert et al., (2002) "Oligonucleotide N3'→P5' phosphoramidates as efficient telomerase inhibitors", Oncogene, vol. 21, pp. 638-642.
Spivak, Jerry L., (2002) "Polycythemia vera: myths, mechanisms, and management", Blood, vol. 100, No. 13, pp. 4272-4290.
Tefferi A, et al. Blood (ASH Annual Meeting Abstracts), Nov. 2013; 122:662.
Wang et al. (2010) "Sequential treatment of CD34+ cells from patients with primary myelofibrosis with chromatin-modifying agents eliminate JAK2V617F-positive NOD/SCID marrow repopulating cells", Blood, vol. 116, No. 26, pp. 5972-5982.
Wang et al., (2014) "JAK2 Inhibitors Do Not Affect Stem Cells Present in the Spleens of Patients with Myelofibrosis. Blood" vol. 124, No. 19, pp. 2987-2995.
Wang X, Hu C, Li Y, et al. 56th ASH Annual Meeting. Dec. 5-9, 2014, San Francisco, CA, 1 page.
Yu et al., (1990) "In vivo alteration of telomere sequences and senescence caused by mutated Tetrahymena telomerase RNAs", Nature, vol. 344, pp. 126-132.
Asai et al., (2003) "A Novel Telomerase Template Antagonist (GRN163) as a Potential Anticancer Agent", Cancer Research, vol. 63, No. 14. pp. 3931-3939.
Herbert et al., (2005) "Lipid Modification of GRN163, an N3'→ P5' Thio-Phosphoramidate Oligonucleotide, Enhances the Potency of Telomerase Inhibition", Oncogene, vol. 24, No. 33, pp. 5262-5268.
Kuykendall et al., (2018) "Between a Rux and a Hard Place: Evaluating Salvage Treatment and Outcomes in Myelofibrosis After Ruxolitinib Discontinuation", Annals of Hematology, vol. 97, pp. 435-441.
Liu and Yuan, (2015) "Bayesian Optimal Interval Designs for Phase I Clinical Trials", Journal of the Royal Statistical Society: Series C: Applied Statistics, pp. 507-523.
Mascarenhas et al., (2020) "Patient Characteristics and Outcomes After Ruxolitinib Discontinuation in Patients with Myelofibrosis", Journal of Medical Economics, vol. 23, No. 7, pp. 721-727.
Mascarenhas et al., (2020) "Potential Disease-Modifying Activity of Imetelstat Demonstrated by Reduction in Cytogenetically Abnormal Clones and Mutation Burden Leads to Clinical Benefits in Relapsed/Refractory Myelofibrosis Patients", Blood, vol. 136, pp. 39-40.
Mascarenhas et al., (2021) "Randomized, Single-Blind, Multicenter Phase II Study of Two Doses of Imetelstat in Relapsed or Refractory Myelofibrosis", Journal of Clinical Oncology, vol. 39, No. 26, pp. 2881-2892.
Newberry et al., (2017) "Clonal Evolution and Outcomes in Myelofibrosis After Ruxolitinib Discontinuation", Blood, vol. 130, No. 9, pp. 1125-1131.
Ross et al., (2021) "Persistence of Myelofibrosis Treated with Ruxolitinib: Biology and Clinical Implications", Haematologica, vol. 106, No. 5, 1244-1253.
Schieber et al., (2019) "Myelofibrosis in 2019; Moving Beyond JAK2 Inhibition", Blood Cancer Journal, vol. 9, No. 9, No. 74, 11 pages.
Tefferi et al. (2021) "Primary Myelofibrosis: 2021 Update on Diagnosis, Risk-Stratification and Management", American Journal of Hematology, vol. 96, No. 1, pp. 145-162.
Vachhani et al., (2022) "Disease Modification in Myelofibrosis: An Elusive Goal?", Journal of Clinical Oncology: Official Journal of The American Society of Clinical Oncology, vol. 40, No. 11, pp. 1147-1154.
Xiao, et al., (2014) "Advances in clinical research on chronic myeloproliferative neoplasms", J. Diagn Concepts Pract, vol. 13, No. 6, pp. 628-631.
Hobbs et al., (2016) "New drugs for myelofibrosis", Expert Opinion on Orphan Drugs, 4(5):521-529.

* cited by examiner

Figure 9, continued

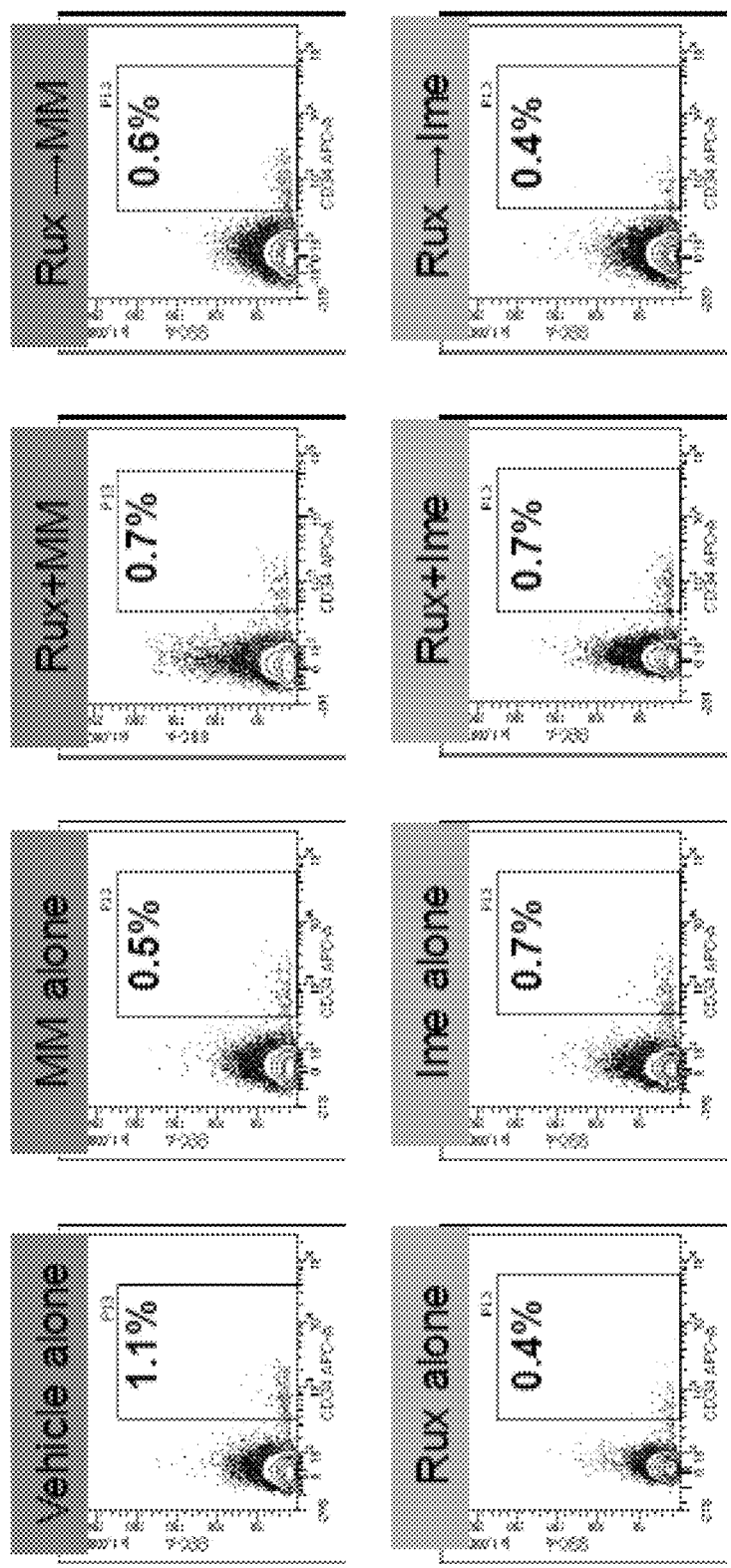
Figure 10, continued

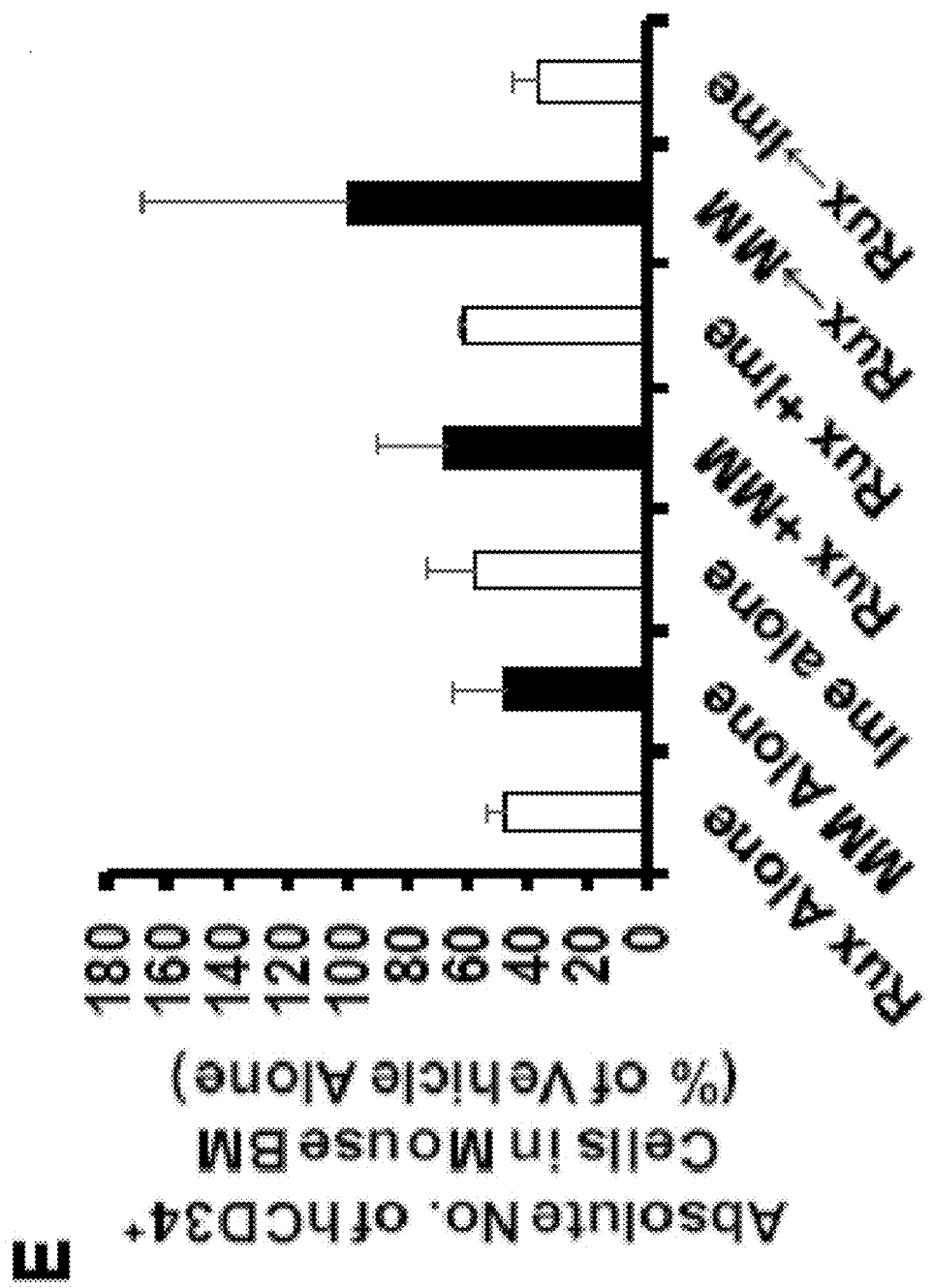
Figure 10, continued

USE OF A JANUS KINASE INHIBITOR AND A TELOMERASE INHIBITOR FOR THE TREATMENT OF MYELOPROLIFERATIVE NEOPLASMS

CROSS-REFERENCE TO RELATED APPLICATIONS

This application claims benefit of priority to U.S. Provisional Application No. 62/930,251, filed Nov. 4, 2019, the disclosure of which is incorporated herein by reference in its entirety.

INTRODUCTION

Myeloproliferative Neoplasms (MPNs) are a group of blood disorders that occur when the body makes too many white or red blood cells, or platelets. This overproduction of blood cells in the bone marrow can create problems for blood flow and lead to various symptoms. MPNs can arise from precursors of the myeloid lineages in the bone marrow. MPNs are characterized by myeloproliferation without dysplasia, bone marrow hypercellularity, and predisposition to thrombosis, hemorrhage, and bone marrow fibrosis.

Imetelstat or imetelstat sodium is a telomerase inhibitor that binds with high affinity to the template region of the RNA component of telomerase. Studies have shown that imetelstat or imetelstat sodium inhibits telomerase activity and is effective against cell proliferation in a multitude of different cancer cell lines and human tumors. Imetelstat or imetelstat sodium has been used in clinical trials of patients with hematologic malignancies. A clinical trial of patients with myelofibrosis showed that imetelstat or imetelstat sodium was able to achieve complete clinical remissions in certain patients. In these patients, imetelstat led to the reversal of bone marrow fibrosis and resulted in morphologic and molecular remission.

SUMMARY

Aspects of the disclosure include methods for treating a myeloproliferative neoplasm. Methods according to certain embodiments include co-administering to a subject a Janus kinase (JAK) inhibitor and a telomerase inhibitor comprising an oligonucleotide and a lipid moiety linked to the 5' and/or 3' end of the oligonucleotide. Methods for inducing apoptosis of a myeloproliferative neoplasm cell by contacting the cell with an amount of a JAK inhibitor and a telomerase inhibitor sufficient to induce apoptosis are also described. Compositions having a JAK inhibitor and a telomerase inhibitor for practicing the subject methods are also provided.

In some embodiments, the JAK inhibitor and the telomerase inhibitor are administered simultaneously. In other embodiments, the JAK inhibitor and the telomerase inhibitor are administered sequentially. In some instances, the telomerase inhibitor is administered to the subject after the JAK inhibitor is administered to the subject. In some instances, the JAK inhibitor is administered to the subject after the telomerase inhibitor is administered to the subject. In one example, the telomerase inhibitor is administered to the subject on the same day as the JAK inhibitor is administered to the subject. In another example, the telomerase inhibitor is administered to the subject within 13 days after the JAK inhibitor is administered to the subject, such as 3 days after the JAK inhibitor is administered to the subject. For instance, the telomerase inhibitor is administered within three days after the last dosage of the JAK inhibitor is administered to the subject. In some instances, the JaK inhibitor is administered to the subject within 13 days after the telomerase inhibitor is administered to the subject. For instance, the JAK inhibitor is administered within three days after the last dosage of the telomerase inhibitor is administered to the subject and twice daily thereafter.

The dosing is administered in cycles of administration of a JAK inhibitor and a telomerase inhibitor. In some embodiments, the cycle is 21 days, in some instances the cycle is 28 or more days. The cycles of drug administration may be repeated for 1, 2, 3, 4, 5, 6, 7, 8 or more than 8 dosage cycles, for a total period of 6 months or 1 year or 2 years or 3 years or 4 years or more.

In certain embodiments, the JAK inhibitor is administered to the subject at a dosage of about 10 mg/day to about 40 mg/day. The JAK inhibitor may be administered to the subject once per day or twice per day. In some instances, the JAK inhibitor is administered to the subject once or twice per day in a cycle for a duration of 30 days, 29 days, 28 days, 27 days, 26 days, 25 days, 24 days, 23 days, 22 days, 21 days, 20 days, 19 days, 18 days, 17 days, 16 days, 15 days, 14 days, 13 days, 12 days, 11 days, 10 days, 9 days, 8 days, 7 days, 6 days, 5 days, 4 days, 3 days or 2 days or 1 day. In some instances, the JAK inhibitor is administered to the subject once per day for a duration of from about 1 day to about 30 days, such as once per day for a duration of from about 1 day to about 28 days, from 1 day to 21 days, from 7 days to 14 days. In other instances, the JAK inhibitor is administered to the subject twice per day for a duration of from about 1 day to about 30 days, such as twice per day for a duration of from about 1 day to about 28 days, from 1 day to 21 days, from 7 days to 14 days.

In certain embodiments, the JAK inhibitor is selected from the group consisting of ruxolitinib, fedratinib, momelotinib and pacritinib or pharmaceutically acceptable salts thereof and combinations thereof. In certain embodiments, the JAK inhibitor is ruxolitinib or pharmaceutically acceptable salt thereof. In certain embodiments, the JAK inhibitor is fedratinib or pharmaceutically acceptable salt thereof. In certain embodiments, the JAK inhibitor is momelotinib or pharmaceutically acceptable salt thereof. In certain embodiments, the JAK inhibitor is pacritinib or pharmaceutically acceptable salt thereof.

In some embodiments, the dosage amount of JAK inhibitor administered to the subject according to methods of the present disclosure may range, such as from about 5 mg/day to about 500 mg/day. In certain embodiments, the JAK inhibitor is ruxolitinib or a pharmaceutically acceptable salt thereof and is administered to a subject at a dosage of. 5 mg twice per day when the subject has a baseline platelet count of less than about $100 \times 10^9$/L platelets; 15 mg twice per day when the subject has a baseline platelet count of from about $100 \times 10^9$/L platelets to about $200 \times 10^9$/L platelets; and 20 mg twice per day when the subject has a baseline platelet count of greater than about $200 \times 10^9$/L platelets.

In certain embodiments, the JAK inhibitor is fedratinib or a pharmaceutically acceptable salt thereof and is administered to a subject at a dosage of 400 mg once per day when the subject has a baseline platelet count of greater than or equal to about $50 \times 10^9$/L. In certain instances, the fedratinib or pharmaceutically acceptable salt thereof is administered to a subject at a dosage of 300 mg once per day. In other instances, the fedratinib or pharmaceutically acceptable salt thereof is administered to a subject at a dosage of 200 mg once per day. In still other instances, the fedratinib or pharmaceutically acceptable salt thereof is administered to a subject at a dosage of 100 mg once per day. In yet other instances, the fedratinib or pharmaceutically acceptable salt thereof is administered to a subject at a dosage of less than 100 mg once per day.

In other embodiments, the JAK inhibitor is momelotinib or a pharmaceutically acceptable salt thereof and is administered to a subject at a dosage of 400 mg once per day. In certain instances, the momelotinib or pharmaceutically acceptable salt thereof is administered to a subject at a dosage of 300 mg once per day. In other instances, the momelotinib or pharmaceutically acceptable salt thereof is administered to a subject at a dosage of 200 mg once per day. In some instances, the momelotinib or a pharmaceutically acceptable salt thereof is administered at a dosage of 150 mg twice per day. In some instances, the momelotinib or a pharmaceutically acceptable salt thereof is administered at a dosage of 100 mg twice per day.

In other embodiments, the JAK inhibitor is pacritinib or a pharmaceutically acceptable salt thereof and is administered to a subject at a dosage of from about 50 mg to about 600 mg once per day, such as from about 100 mg to about 500 mg once per day, such as from about 150 mg to about 400 mg once per day, and including from about 200 mg to about 350 mg once per day. In certain instances, the pacritinib or pharmaceutically acceptable salt is administered to a subject at a dosage of from about 50 mg to about 600 mg twice per day, such as from about 100 mg to about 500 mg twice per day, such as from about 150 mg to about 400 mg twice per day, and including from about 200 mg to about 350 mg twice per day. In other instances, the pacritinib or pharmaceutically acceptable salt is administered to a subject at a dosage of 100 mg once per day, or from about 100 mg twice per day or from 200 mg twice per day.

Methods according to certain embodiments also include determining the baseline platelet count of the subject before administering the JAK inhibitor to subject. In these embodiments, methods may include determining a baseline platelet count of the subject and determining an amount of the JAK inhibitor for administering to the subject based on the baseline platelet count of the subject.

The dosage amount of telomerase inhibitor administered to the subject may range, such as from about 4.0 mg/kg to about 10 mg/kg, from about 7.5 mg/kg to 9.4 mg/kg. In certain embodiments, the telomerase inhibitor is administered to the subject at a dosage of 4.0 mg/kg, 4.1 mg/kg, 4.2 mg/kg, 4.3 mg/kg, 4.4 mg/kg, 4.5 mg/kg, 4.6 mg/kg, 4.7 mg/kg, 4.8 mg/kg, 4.9 mg/kg, 5.0 mg/kg, 5.1 mg/kg, 5.2 mg/kg, 5.3 mg/kg, 5.4 mg/kg, 5.5 mg/kg, 5.6 mg/kg, 5.7 mg/kg, 5.8 mg/kg, 5.9 mg/kg, 6.0 mg/kg, 6.1 mg/kg, 6.2 mg/kg, 6.3 mg/kg, 6.4 mg/kg, 6.5 mg/kg, 6.6 mg/kg, 6.7 mg/kg, 6.8 mg/kg, 6.9 mg/kg, 7.0 mg/kg, 7.1 mg/kg, 7.2 mg/kg, 7.3 mg/kg, 7.4 mg/kg, 7.5 mg/kg, 7.6 mg/kg, 7.7 mg/kg, 7.8 mg/kg, 7.9 mg/kg, 8.0 mg/kg, 8.1 mg/kg, 8.2 mg/kg, 8.3 mg/kg, 8.4 mg/kg, 8.5 mg/kg, 8.6 mg/kg, 8.7 mg/kg, 8.8 mg/kg, 8.9 mg/kg, 9.0 mg/kg, 9.1 mg/kg, 9.2 mg/kg, 9.3 mg/kg, 9.4 mg/kg, 9.5 mg/kg, 9.6 mg/kg, 9.7 mg/kg, 9.8 mg/kg, 9.9 mg/kg, 10.0 mg/kg.

The dosage of the telomerase inhibitor may be administered to the subject in a cycle where the telomerase inhibitor is administered once every, week, once every two weeks (14 days), once every three weeks (21 days) or once every four weeks (28 days), once every 6 weeks, once every 8 weeks, once every 10 weeks, once every 12 weeks. In certain embodiments, imetelstat or a pharmaceutically acceptable salt may be administered for 1, 2, 3, 4, 5, 6, 7, 8 or more than 8 dosage cycles. In certain embodiments, each cycle includes: intravenous administration of about 4-10 mg/kg imetelstat or a pharmaceutically acceptable salt once every three weeks, intravenous administration of about 4-10 mg/kg imetelstat or imetelstat sodium once every four weeks, intravenous administration of about 4-10 mg/kg imetelstat or imetelstat sodium once every two weeks, or intravenous administration of about 7.5-9.4 mg/kg imetelstat or imetelstat sodium once every three weeks. In certain instance, each dosage cycle includes intravenous administration of about 7.5-9.4 mg/kg imetelstat or imetelstat sodium once every four weeks. In some cases, each dosage cycle includes intravenous administration of about 9.4 mg/kg imetelstat or imetelstat sodium about once every three weeks.

In some instances, the oligonucleotide of the telomerase inhibitor includes at least one N3'→P5' thiophosphoramidate internucleoside linkage. In some instances, the lipid moiety of the telomerase inhibitor is linked to the 5' and/or 3' end of the oligonucleotide via a linker, such as a glycerol or aminoglycerol linker. In some instances, the lipid moiety of the telomerase inhibitor is a palmitoyl (C16) moiety. In certain embodiments, the telomerase inhibitor is imetelstat or a pharmaceutically acceptable salt thereof, such as imetelstat sodium.

In certain embodiments, treating a myeloproliferative neoplasm includes treating a subject with a 21-day administrative cycle of ruxolitinib or a pharmaceutically acceptable salt thereof and imetelstat or a pharmaceutically acceptable salt thereof where methods include administering the ruxolitinib or pharmaceutically acceptable salt thereof once or twice per day for 21 days and administering the imetelstat or pharmaceutically acceptable salt thereof to the subject on the first day of the 21-day administration cycle. (i.e., the ruxolitinib or a pharmaceutically acceptable salt thereof and imetelstat or pharmaceutically acceptable salt thereof are both administered to the subject on first day of the 21-day cycle). In certain instances, methods include a 21-day administrative cycle of ruxolitinib or a pharmaceutically acceptable salt thereof and imetelstat or a pharmaceutically acceptable salt thereof where the ruxolitinib or pharmaceutically acceptable salt thereof is administered once per day for 21 days and the imetelstat or pharmaceutically acceptable salt thereof is administered on the first day of the 21-day cycle. In other instances, methods include a 21-day administrative cycle of ruxolitinib or a pharmaceutically acceptable salt thereof and imetelstat or a pharmaceutically acceptable salt thereof where the ruxolitinib or pharmaceutically acceptable salt thereof is administered twice per day for 21 days and the imetelstat or pharmaceutically acceptable salt thereof is administered on the first day of the 21-day cycle. The 21-day administration cycle of administering ruxolitinib or a pharmaceutically acceptable salt thereof and imetelstat or a pharmaceutically acceptable salt thereof according to these embodiments can be repeated 1 or more times, such as 2 or more times, such as 3 or more times, such as 4 or more times, such as 5 or more times, such as 6 or more time, such as 7 or more times, such as 8 or more times, such as 9 or more times and including 10 or more times. Where the 21-day administration cycle of ruxolitinib and imetelstat is repeated 1 or more times, the duration between each 21-day administration cycle may be 0 days or more, such as 1 day or more, such as 2 days or more, such as 3 days or more, such as 4 days or more, such as 5 days or more, such as 6 days or more and including 7 days or more. Depending on the number of 21-day administration cycles of ruxolitinib and imetelstat employed and the duration between each cycle, the duration of treatment of the subject according to these embodiments may be about 1.5 months or more, such as 3 months or more, such as 6 months or more, such as 1 year or more, such as 2 years or more, such as 3 years or more, such as 4 years or more, such as 5 years or more, such as 6 years or more, such as 7 years or more, such as 8 years or more, such as 9 years or more and including for 10 years or more.

In certain embodiments, treating a myeloproliferative neoplasm includes treating a subject with a 28-day administrative cycle of ruxolitinib or a pharmaceutically acceptable salt thereof and imetelstat or a pharmaceutically acceptable salt thereof. In these embodiments, methods include administering the ruxolitinib or pharmaceutically acceptable salt thereof once or twice per day for 28 days and administering the imetelstat or pharmaceutically acceptable salt thereof to the subject on the first day of the 28 day cycle. (i.e., the ruxolitinib or a pharmaceutically acceptable salt thereof and imetelstat or pharmaceutically acceptable salt thereof are both administered to the subject on first day of the 28-day cycle). In certain instances, methods include a 28-day administrative cycle of ruxolitinib or a pharmaceutically acceptable salt thereof and imetelstat or a pharmaceutically acceptable salt thereof where the ruxolitinib or pharmaceutically acceptable salt thereof is administered once per day for 28 days and the imetelstat or pharmaceutically acceptable salt thereof is administered on the first day of the 28-day cycle. In other instances, methods include a 28-day administrative cycle of ruxolitinib or a pharmaceutically acceptable salt thereof and imetelstat or a pharmaceutically acceptable salt thereof where the ruxolitinib or pharmaceutically acceptable salt thereof is administered twice per day for 28 days and the imetelstat or pharmaceutically acceptable salt thereof is administered on the first day of the 28-day cycle.

The 28-day administration cycle of administering ruxolitinib or a pharmaceutically acceptable salt thereof and imetelstat or a pharmaceutically acceptable salt thereof according to these embodiments can be repeated 1 or more times, such as 2 or more times, such as 3 or more times, such as 4 or more times, such as 5 or more times, such as 6 or more time, such as 7 or more times, such as 8 or more times, such as 9 or more times and including 10 or more times. Where the 28-day administration cycle of ruxolitinib and imetelstat is repeated 1 or more times, the duration between each 28-day administration cycle may be 0 days or more, such as 1 day or more, such as 2 days or more, such as 3 days or more, such as 4 days or more, such as 5 days or more, such as 6 days or more and including 7 days or more. Depending on the number of 28-day administration cycles of ruxolitinib and imetelstat employed and the duration between each cycle, the duration of treatment of the subject according to these embodiments may be about 2 months or more, such as 4 months or more, such as 6 months or more, such as 1 year or more, such as 2 years or more, such as 3 years or more, such as 4 years or more, such as 5 years or more, such as 6 years or more, such as 7 years or more, such as 8 years or more, such as 9 years or more and including for 10 years or more.

In certain embodiments, treating a myeloproliferative neoplasm includes treating a subject with an administration cycle of ruxolitinib or a pharmaceutically acceptable salt thereof and imetelstat or a pharmaceutically acceptable salt thereof where the ruxolitinib or pharmaceutically acceptable salt thereof is administered to the subject once or twice per day for 14 days or 21 days followed by administering one dose or more of imetelstat or a pharmaceutically acceptable salt thereof to the subject from 1 day to 7 days after the last administered dosage of ruxolitinib or pharmaceutically acceptable salt thereof for that administration cycle. In one example, methods include an administration cycle where the ruxolitinib or pharmaceutically acceptable salt thereof is administered to the subject once per day for 14 days followed by administering the one dose or more of imetelstat or pharmaceutically acceptable salt thereof from 1 day to 7 days after the last administered dosage of ruxolitinib or pharmaceutically acceptable salt thereof. In another example, methods include an administration cycle where the ruxolitinib or pharmaceutically acceptable salt thereof is administered to the subject once per day for 21 days followed by administering one dose or more of imetelstat or pharmaceutically acceptable salt thereof from 1 day to 7 days after the last administered dosage of ruxolitinib or pharmaceutically acceptable salt thereof. In yet another example, methods include an administration cycle where the ruxolitinib or pharmaceutically acceptable salt thereof is administered to the subject twice per day for 14 days followed by administering one dose or more of imetelstat or pharmaceutically acceptable salt thereof from 1 day to 7 days after the last administered dosage of ruxolitinib or pharmaceutically acceptable salt thereof. In still another example, methods include an administration cycle where the ruxolitinib or pharmaceutically acceptable salt thereof is administered to the subject twice per day for 21 days followed by administering one dose or more of imetelstat or pharmaceutically acceptable salt thereof from 1 day to 7 days after the last administered dosage of ruxolitinib or pharmaceutically acceptable salt thereof. In these embodiments, One dose or more of imetelstat or pharmaceutically acceptable salt thereof is administered to the subject from 1 day to 7 days after the last administered dosage of ruxolitinib or pharmaceutically acceptable salt thereof, such as 1 day after, such as 2 days after, such as 3 days after, such as 4 days after, such as 5 days after, such as 6 days after and including administering one dose of imetelstat or pharmaceutically acceptable salt thereof 7 days after the last administered dosage of ruxolitinib or pharmaceutically acceptable salt thereof. The administration cycle of ruxolitinib or a pharmaceutically acceptable salt thereof and imetelstat or a pharmaceutically acceptable salt thereof according to these embodiments can be repeated 1 or more times, such as 2 or more times, such as 3 or more times, such as 4 or more times, such as 5 or more times, such as 6 or more time, such as 7 or more times, such as 8 or more times, such as 9 or more times and including 10 or more times.

In certain embodiments, treating a myeloproliferative neoplasm includes treating a subject with a 21-day administrative cycle of imetelstat or a pharmaceutically acceptable salt thereof and ruxolitinib or a pharmaceutically acceptable salt thereof where methods include administering imetelstat or a pharmaceutically acceptable salt thereof to the subject on the first day of the 21-day administration cycle followed by administering ruxolitinib or a pharmaceutically acceptable salt thereof to the subject once or twice per day on each subsequent day of the 21-day cycle (i.e., the imetelstat or pharmaceutically acceptable salt thereof is administered to the subject on first day of the 21-day cycle and the ruxolitinib or a pharmaceutically acceptable salt thereof is administered once or twice per day on days 2-21 of the 21-day administration cycle). In certain instances, methods include administering imetelstat or a pharmaceutically acceptable salt thereof to the subject on the first day of the 21-day administration cycle followed by administering ruxolitinib or a pharmaceutically acceptable salt thereof to the subject once per day on each subsequent day of the 21-day cycle. In other instances, methods include administering imetelstat or a pharmaceutically acceptable salt thereof to the subject on the first day of the 21-day administration cycle followed by administering ruxolitinib or a pharmaceutically acceptable salt thereof to the subject twice per day on each subsequent day of the 21-day cycle. The 21-day administration cycle of administering imetelstat or a pharmaceutically acceptable salt thereof followed by ruxolitinib or a pharmaceutically acceptable salt thereof according to these embodiments can be repeated 1 or more times, such as 2 or more times, such as 3 or more times, such as 4 or more times, such as 5 or more times, such as 6 or more time, such as 7 or more times, such as 8 or more times, such as 9 or more times and including 10 or more times. Where the 21-day administration cycle of imetelstat and ruxolitinib is repeated 1 or more times, the duration between each 21-day administration cycle may be 0 days or more, such as 1 day or more, such as 2 days or more, such as 3 days or more, such as 4 days or more, such as 5 days or more, such as 6 days or more and including 7 days or more. Depending on the number of 21-day administration cycles of imetelstat and ruxolitinib employed and the duration between each cycle, the duration of treatment of the subject according to these embodiments may be about 1.5 months or more, such as 3 months or more, such as 6 months or more, such as 1 year or more, such as 2 years or more, such as 3 years or more, such as 4 years or more, such as 5 years or more, such as 6 years or more, such as 7 years or more, such as 8 years or more, such as 9 years or more and including for 10 years or more.

In other embodiments, treating a myeloproliferative neoplasm includes treating a subject with a 28-day administrative cycle of imetelstat or a pharmaceutically acceptable salt thereof and ruxolitinib or a pharmaceutically acceptable salt thereof where methods include administering imetelstat or a pharmaceutically acceptable salt thereof to the subject on the first day of the 28-day administration cycle followed by administering ruxolitinib or a pharmaceutically acceptable salt thereof to the subject once or twice per day on each subsequent day of the 28-day cycle (i.e., the imetelstat or pharmaceutically acceptable salt thereof is administered to the subject on first day of the 28-day cycle and the ruxolitinib or a pharmaceutically acceptable salt thereof is administered once or twice per day on days 2-28 of the 28-day administration cycle). In certain instances, methods include administering imetelstat or a pharmaceutically acceptable salt thereof to the subject on the first day of the 28-day administration cycle followed by administering ruxolitinib or a pharmaceutically acceptable salt thereof to the subject once per day on each subsequent day of the 28-day cycle. In other instances, methods include administering imetelstat or a pharmaceutically acceptable salt thereof to the subject on the first day of the 28-day administration cycle followed by administering ruxolitinib or a pharmaceutically acceptable salt thereof to the subject twice per day on each subsequent day of the 28-day cycle. The 28-day administration cycle of administering imetelstat or a pharmaceutically acceptable salt thereof followed by ruxolitinib or a pharmaceutically acceptable salt thereof according to these embodiments can be repeated 1 or more times, such as 2 or more times, such as 3 or more times, such as 4 or more times, such as 5 or more times, such as 6 or more time, such as 7 or more times, such as 8 or more times, such as 9 or more times and including 10 or more times. Where the 28-day administration cycle of imetelstat and ruxolitinib is repeated 1 or more times, the duration between each 28-day administration cycle may be 0 days or more, such as 1 day or more, such as 2 days or more, such as 3 days or more, such as 4 days or more, such as 5 days or more, such as 6 days or more and including 7 days or more. Depending on the number of 28-day administration cycles of imetelstat and ruxolitinib employed and the duration between each cycle, the duration of treatment of the subject according to these embodiments may be about 2 months or more, such as 4 months or more, such as 6 months or more, such as 1 year or more, such as 2 years or more, such as 3 years or more, such as 4 years or more, such as 5 years or more, such as 6 years or more, such as 7 years or more, such as 8 years or more, such as 9 years or more and including for 10 years or more.

In other embodiments, methods include administering ruxolitinib or a pharmaceutically acceptable salt thereof for a predetermined duration (from 1 days to 21 days), discontinuing administration of the ruxolitinib or pharmaceutically acceptable salt thereof and administering imetelstat within 7 days (e.g., 2 days, 1 day or on the same day) of the last dosage of ruxolitinib or pharmaceutically acceptable salt thereof administered to the subject. This administration cycle may be repeated, such as 2 or more times, such as 3 or more times, such as 4 or more times, such as 5 or more times, such as 6 or more time, such as 7 or more times, such as 8 or more times, such as 9 or more times and including 10 or more times.

In some embodiments, the myeloproliferative neoplasm is myelofibrosis (MF), such as primary myelofibrosis, or myelofibrosis following previous ET or PV (post-ETMF or post-PVMF). In other embodiments, the myeloproliferative neoplasm includes Essential Thrombocythemia (ET), Polycythemia vera (PV), Chronic Myelogenous Leukemia (CML), chronic neutrophilic leukemia, chronic eosinophilic leukemia and acute myelogenous leukemia (AML). In other embodiments, the myeloproliferative neoplasm is myelodysplastic syndromes (MDS). In still other embodiments, the myeloproliferative neoplasm is myelodysplastic syndromes (MDS) with isolated del (5q). Myelodysplastic syndromes (MDS) includes diseases such as, refractory anemia, refractory anemia with excess blasts, refractory cytopenia with multilineage dysplasia, refractory cytopenia with unilineage dysplasia, and chronic myelomonocytic leukemia (CMML). Methods according certain embodiments also include diagnosing a subject has having a myeloproliferative neoplasm. In one example, methods include diagnosing the subject has having myelofibrosis, such as primary myelofibrosis. In some embodiments, the subject has not previously been administered a JAK inhibitor (i.e., is JAK inhibitor naïve). In other embodiments, the subject has not previously been administered a telomerase inhibitor (e.g., is telomerase inhibitor naïve). In yet other embodiments, the subject has not previously been administered a JAK inhibitor or a telomerase inhibitor (i.e., is both JAK inhibitor naïve and telomerase inhibitor naïve).

alone, mismatched oligonucleotide (MM, 1.8 uM) or imetelstat (Ime, 1.8 uM) alone, Rux and MM or Ime simultaneously and sequentially as described in the text. The cells were exposed to Rux for 3 days and to MM or Ime for 7 days. Cells generated in the cultures were phenotypically characterized and were assayed for HPCs. The percentages of the absolute number of Lin-CD34$^+$ cells (FIG. 4, panel A), all classes of assayable HPCs (FIG. 4, panel B), as well as CD15$^+$CD34$^-$ (FIG. 4, panel C) cells generated in the cultures of normal CD34$^+$ cells exposed to various treatments relative to that generated in the cultures exposed to corresponding vehicle alone are shown. n=3. P all >0.05, Cultures containing vehicle alone vs. cultures containing Rux; Cultures containing MM vs. corresponding cultures containing Ime.

Figure 5:
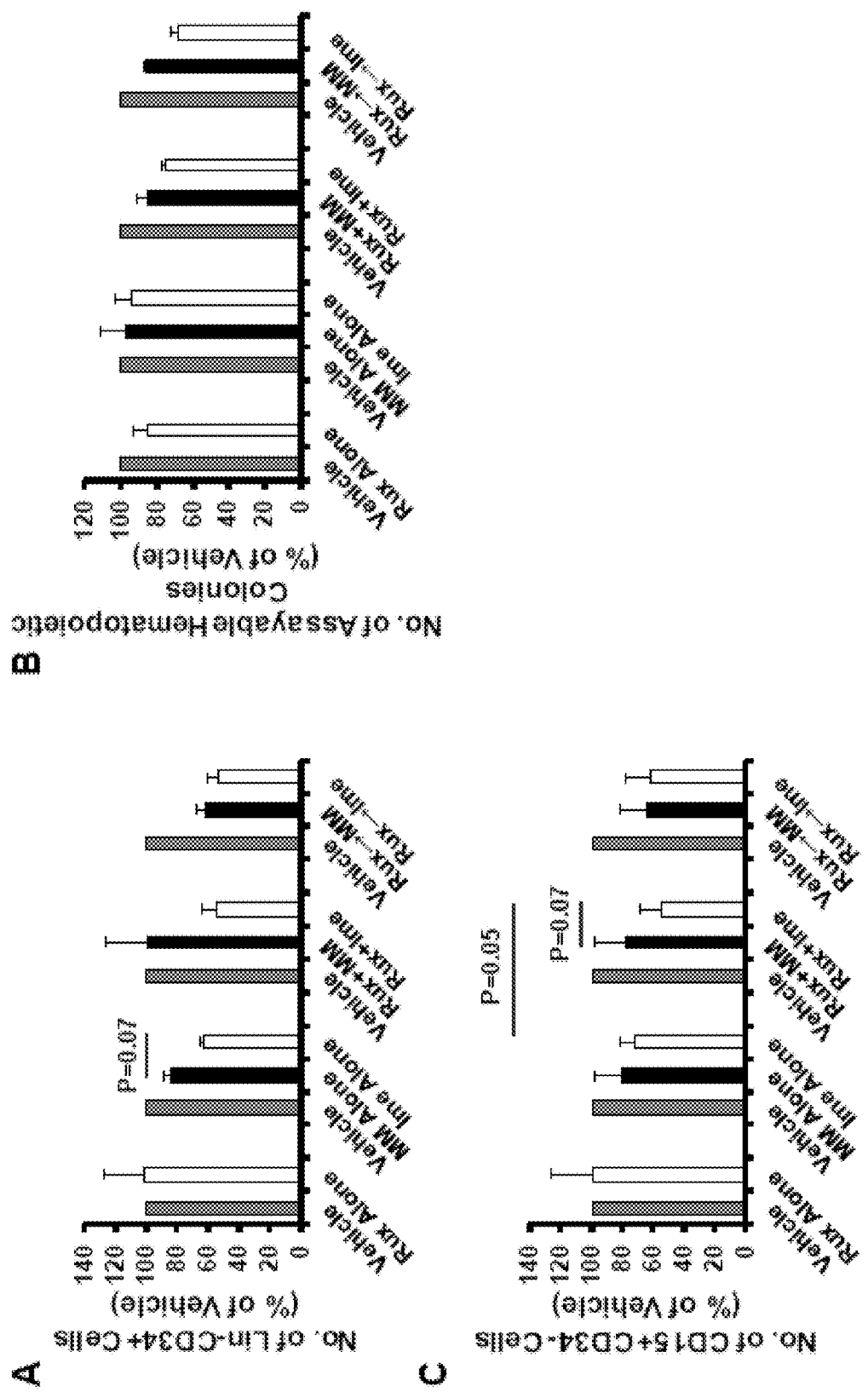

FIG. 5 depicts lack of additive inhibitory effect against normal HSC/HPC observed with long-term, combination treatment in vitro with imetelstat and ruxolitinib according to certain embodiments. Normal CB CD34$^+$ cells were treated with vehicle alone, ruxolitinib (Rux, 50 nM) alone, mismatched oligonucleotide (MM, 1.8 uM) or imetelstat (Ime, 1.8 uM) alone, Rux and MM or Ime simultaneously and sequentially as described in the text. The cells were exposed to Rux for 3 days and to MM or Ime for 14 days. The percentages of the absolute number of Lin-CD34$^+$ cells (FIG. 5, panel A), all classes of assayable HPCs (FIG. 5, panel B), as well as CD15$^+$CD34$^-$ (FIG. 5, panel C) cells generated in the cultures of normal CD34$^+$ cells exposed to various treatments relative to that generated in the cultures exposed to corresponding vehicle alone are shown. n=3. P all >0.05, Cultures containing vehicle alone vs. cultures containing Rux; Cultures containing MM vs. corresponding cultures containing Ime unless indicated.

Figure 6:
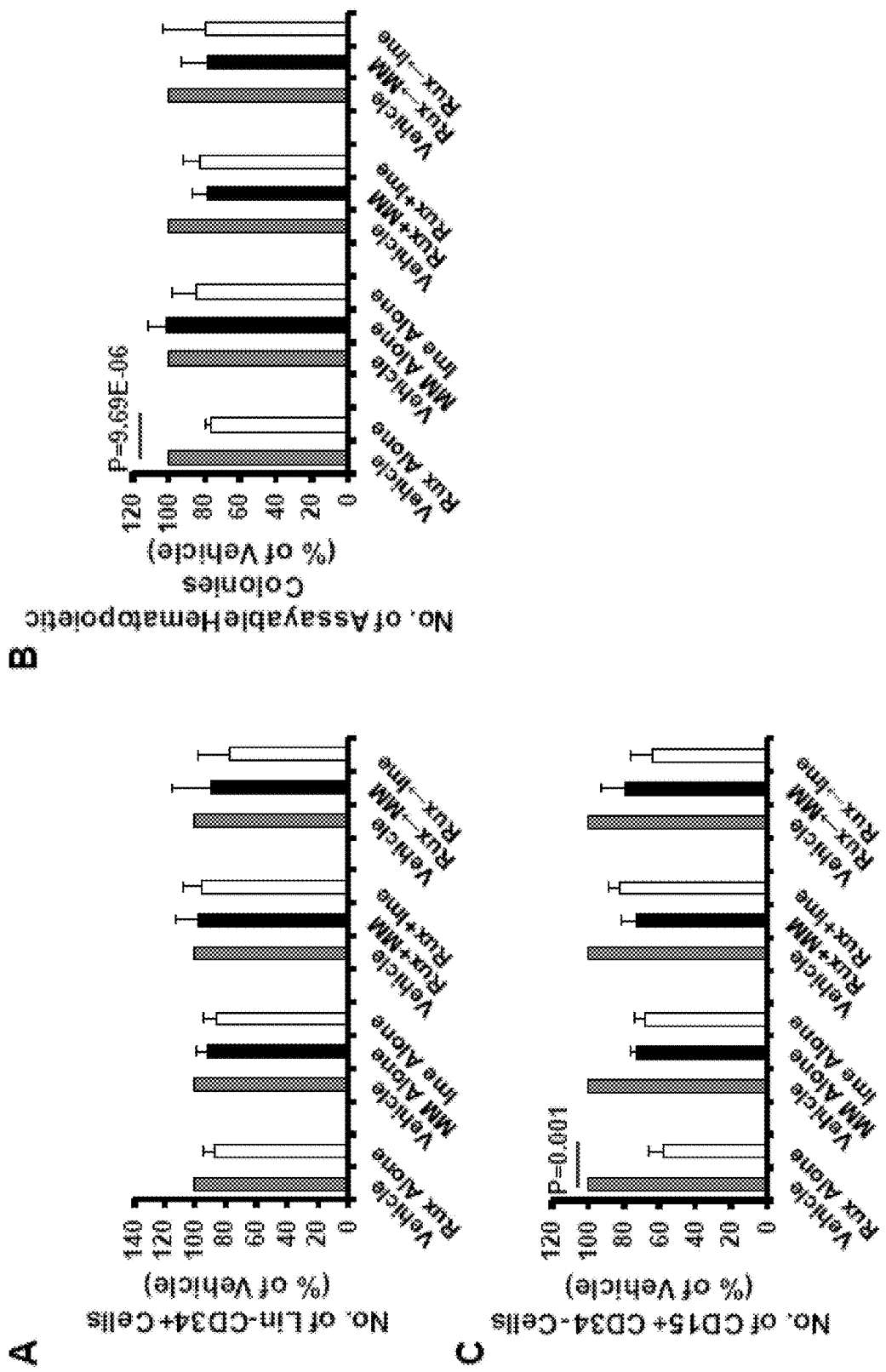

FIG. 6 depicts lack of additive inhibitory effect on MF HSCs/HPCs by simultaneous or sequential short-term combination treatment in vitro with imetelstat and ruxolitinib according to certain embodiments. MF splenic CD34$^+$ cells were treated with the two drugs in an identical fashion as CB CD34$^+$ cells. The cells were exposed to Rux for 3 days and to MM or Ime for 7 days. Cells generated after the culture were phenotypically characterized and were assayed for HPCs. The percentages of the absolute number of Lin-CD34$^+$ cells (FIG. 6, panel A), all classes of assayable HPCs (FIG. 6, panel B), as well as CD15$^+$CD34$^-$ (FIG. 6, panel C) cells generated in the cultures of MF splenic CD34$^+$ cells exposed to various treatments relative to that generated in the cultures exposed to corresponding vehicle alone are shown. JAK2V617F+MF, n=3; JAK2V617F−MF, n=4. P all >0.05, Cultures containing vehicle alone vs. cultures containing Rux; Cultures containing MM vs. corresponding cultures containing Ime unless indicated.

Figure 7:
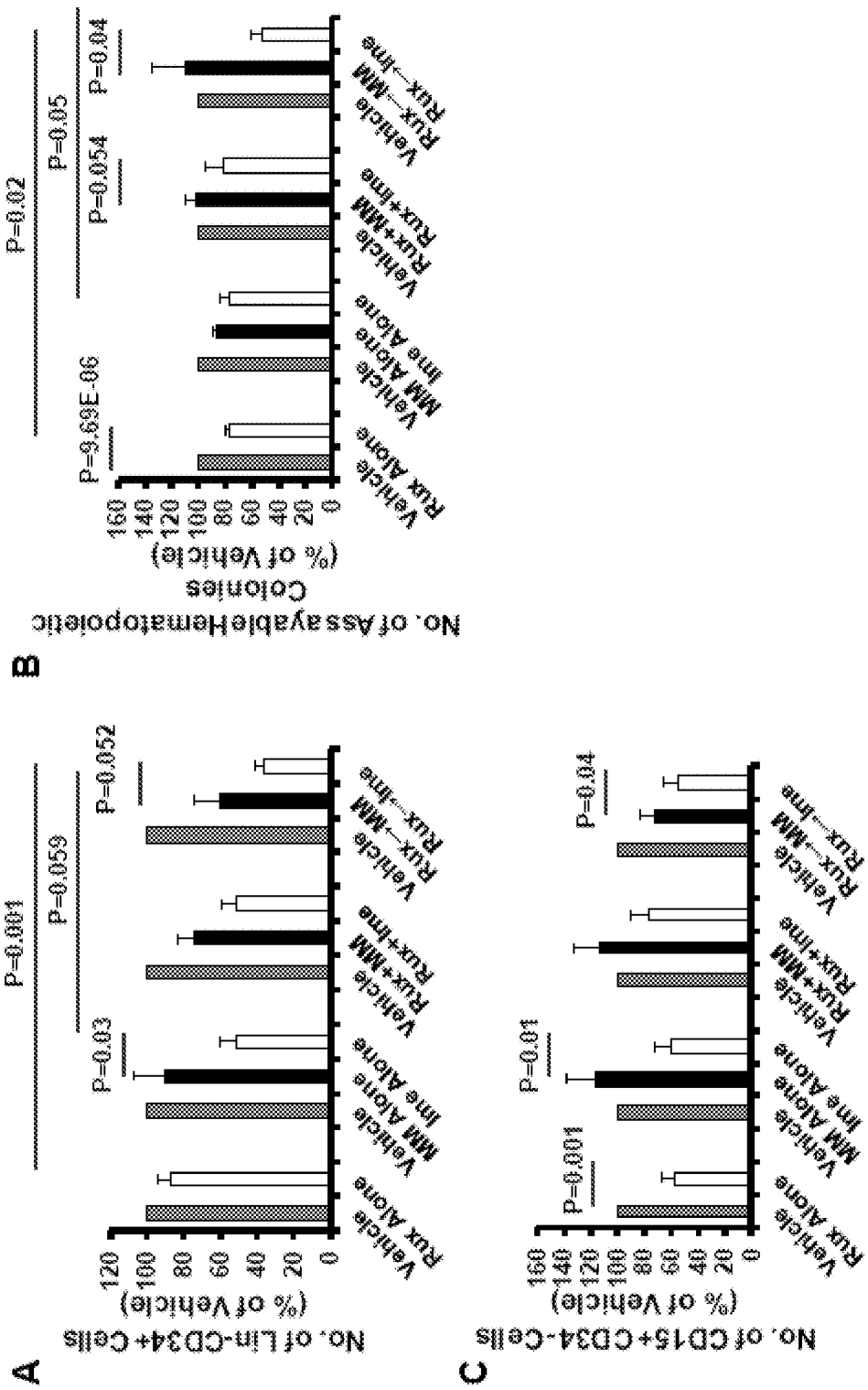

FIG. 7 depicts additive inhibitory activity against MF HSCs/HPCs with sequential long-term combination treatment in vitro with imetelstat and ruxolitinib according to certain embodiments. MF splenic CD34$^+$ cells were treated with the two drugs alone and in combination in an identical fashion as CB CD34$^+$ cells. The cells were exposed to Rux for 3 days and to MM or Ime for 14 days. Cells generated after the culture were phenotypically characterized and were assayed for HPCs. The percentages of the absolute number of Lin-CD34$^+$ cells (FIG. 7, panel A), all classes of assayable HPCs (FIG. 7, panel B), as well as CD15$^+$CD34$^-$ (FIG. 7, panel C) cells generated in the cultures of MF splenic CD34$^+$ cells exposed to various treatments relative to that generated in the cultures exposed to corresponding vehicle alone are shown. JAK2V617F$^+$ MF, n=3; JAK2V617F$^-$ MF, n=4. P values are as indicated, otherwise P >0.05, Panel A: vehicle vs. Rux alone, Rux+MM vs. Rux+Ime; Panel C: Rux+MM vs. Rux+Ime.

Figure 8:
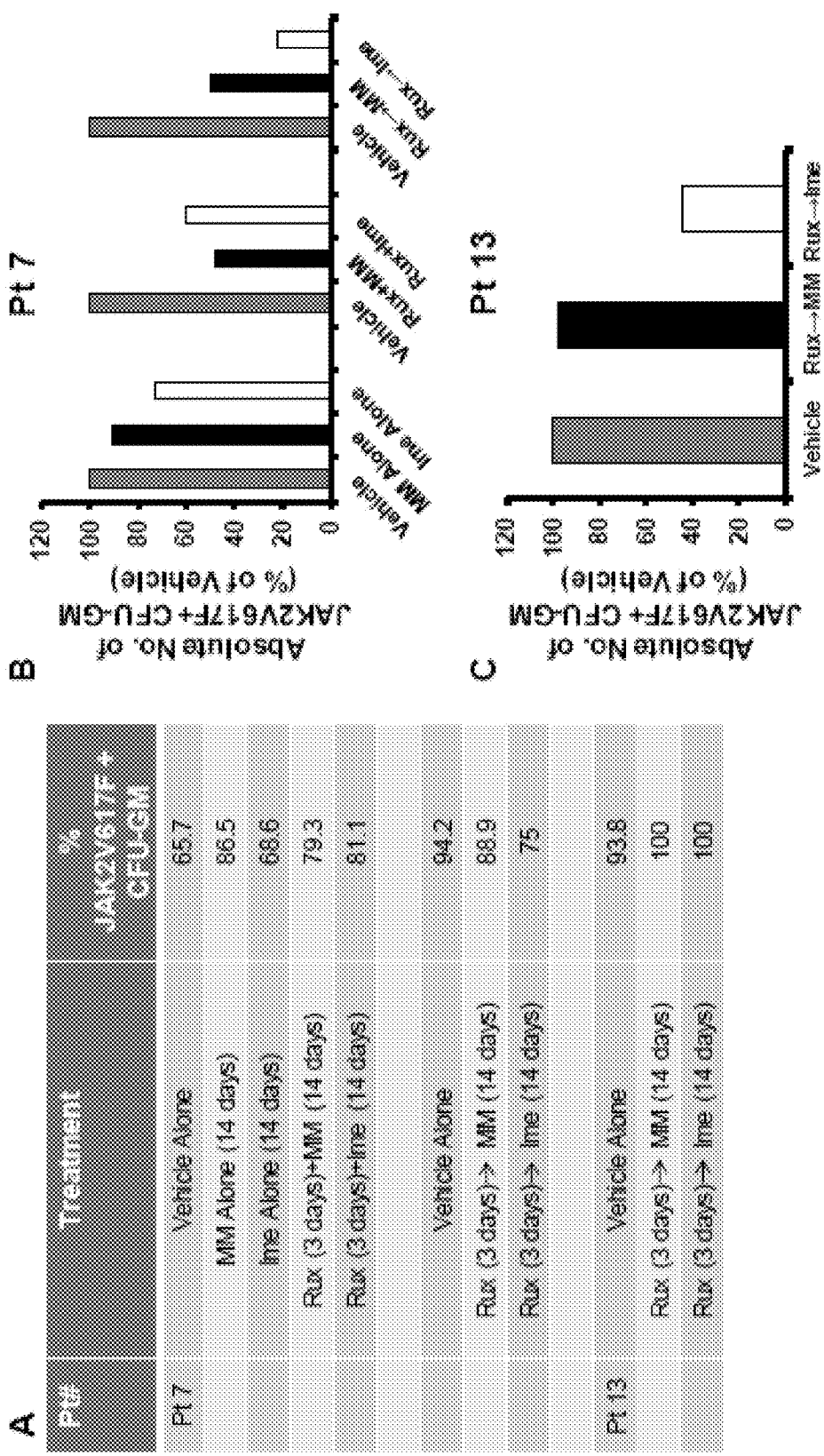

FIG. 8 depicts reduction of JAK2V617F$^+$ hematopoietic progenitor cells with sequential long-term combination treatment in vitro with imetelstat and ruxolitinib according to certain embodiments. (FIG. 8, panel A) Individual colonies (CFU-GM) from 2 JAK2V617F$^+$ MF patients exposed to various treatments were plucked and genotyped for the JAK2V617F using a nested allele-specific polymerase chain reaction (PCR). The percentage of JAK2V617F$^+$ CFU-GM was then determined. (FIG. 8, panels B and C) The absolute numbers of JAK2V617F$^+$ CFU-GM were calculated by multiplying the total number of CFU-GM generated in each culture by the percentage of JAK2V617F$^+$ CFU-GM shown in Panel A. Sequential long-term combination treatment of splenic CD34$^+$ cells from both patients with of Rux followed by imetelstat has an additive inhibitory activity against malignant MF HPCs.

Figure 9:
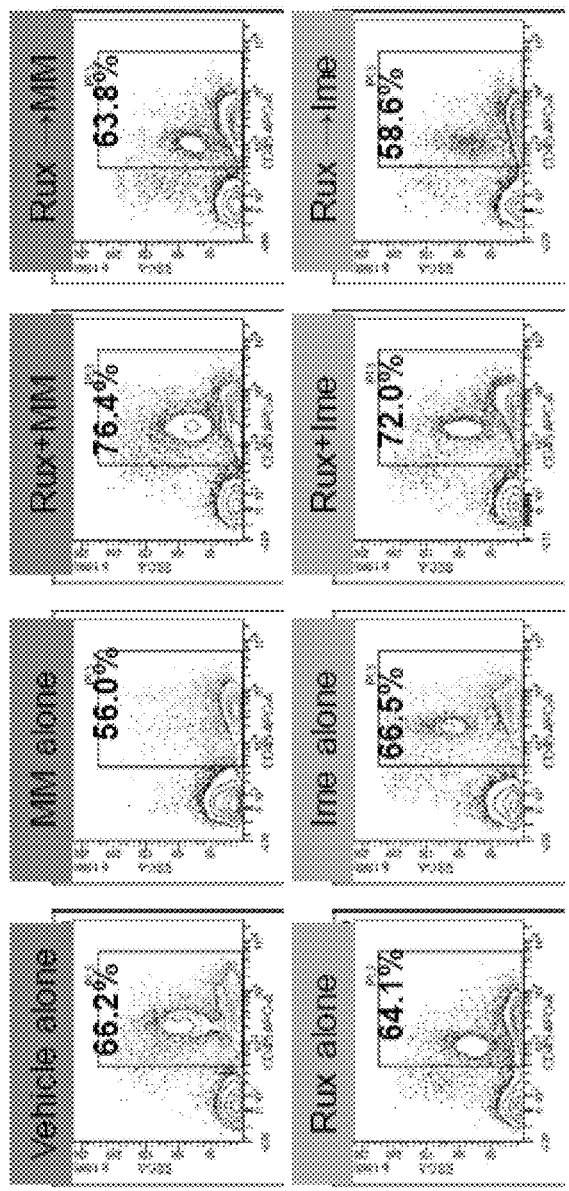
Figure 9:
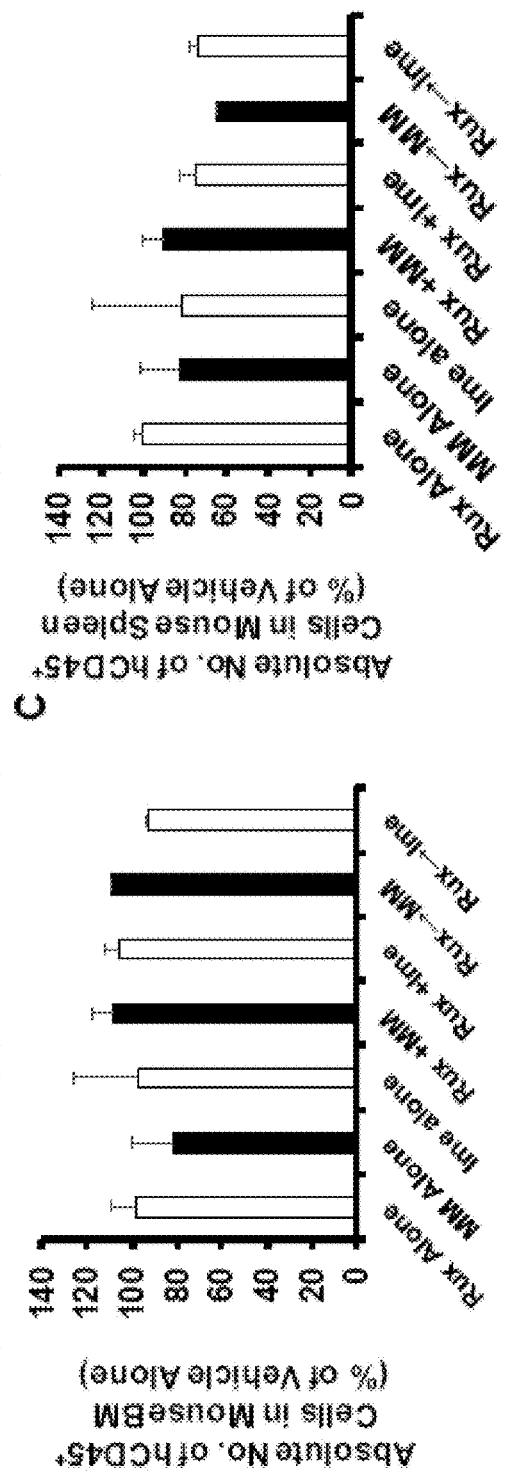
Figure 10:
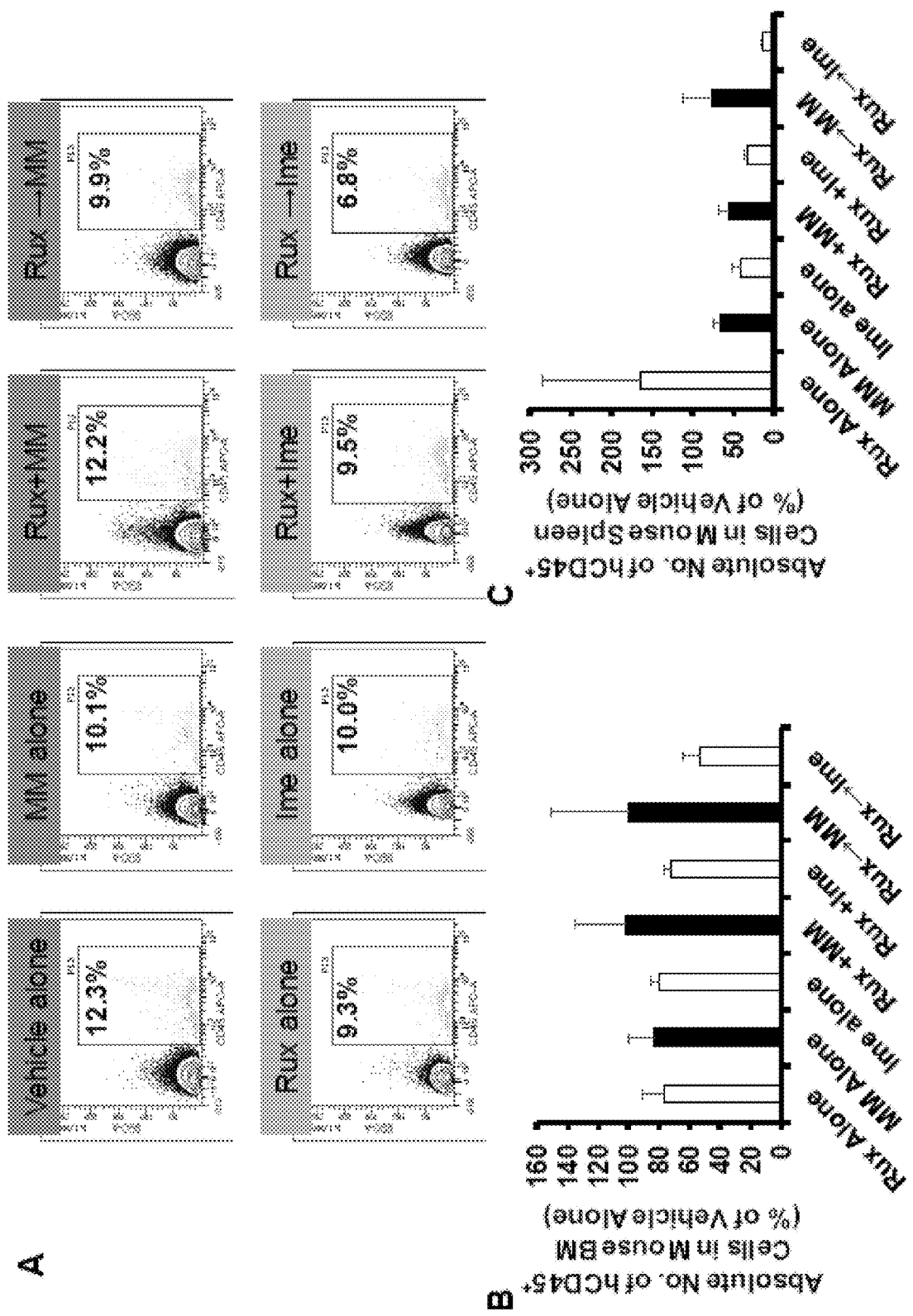

FIG. 9 depicts the lack of effect on normal NSG repopulating cells (SRC) by simultaneous or sequential combination treatment in vivo with imetelstat and ruxolitinib according to certain embodiments. (FIG. 9, panels A and D) Representative FACS plots showing human (h) CD45$^+$ chimerism (FIG. 9, panel A) and hCD34$^+$ cells (FIG. 9, panel D) generated in the marrow of mice are shown. (FIG. 9, panels B-C; FIG. 9, panels E-F) The absolute number of hCD45$^+$ (FIG. 9, panels B-C) and hCD34$^+$ cells (FIG. 9, panels E-F) generated in the marrow (FIG. 9, panels B and E) and spleen (FIG. 9, panels C and F) of NSG mice 4 months after the transplantation. NSG mice were transplanted with normal CB CD34$^+$ cells and were treated with various drugs alone or in combination one-week post transplantation. These treatments resulted in a minimal reduction (hCD45$^+$ cells in the spleen: Rux+Ime; hCD34+ cells in the spleen: Ime alone, Rux+Ime) in the degree of hCD45+ cell chimerism and hCD34+ cell generation in marrows and spleens of the recipient mice FIG. 10 depicts the additive effect on depleting myelofibrosis NSG repopulating cells (SRC) with combination treatment in vivo with imetelstat and ruxolitinib according to certain embodiments. (FIG. 10, panels A and D) FACS plots showing human (h) CD45$^+$ cell chimerism (FIG. 10, panel A) and hCD34$^+$ cells (FIG. 10, panel D) generated in the marrow of mice are shown. (FIGS. 10, panels B-C; FIG. 10, panel E) The absolute number of hCD45$^+$ (FIG. 10, panels B-C) and hCD34$^+$ cells (FIG. 10, panel E) generated in the marrow (FIG. 10, panels B and E) and spleen (FIG. 10, panel C) of NSG mice 4 months after the transplantation. The percentages of the absolute number of hCD45$^+$ and hCD34$^+$ cells generated in marrows and spleens of mice receiving each drug treatment relative to that generated in mice receiving vehicle alone are shown. NSG mice were transplanted with splenic CD34$^+$ cells of Pt5 and were treated with various drugs alone or in combination one week after the transplantation as described in the text. Sequential treatment with Rux followed by imetelstat had additive activity in depleting MF long-term SRC of Pt5.

Figure 11:
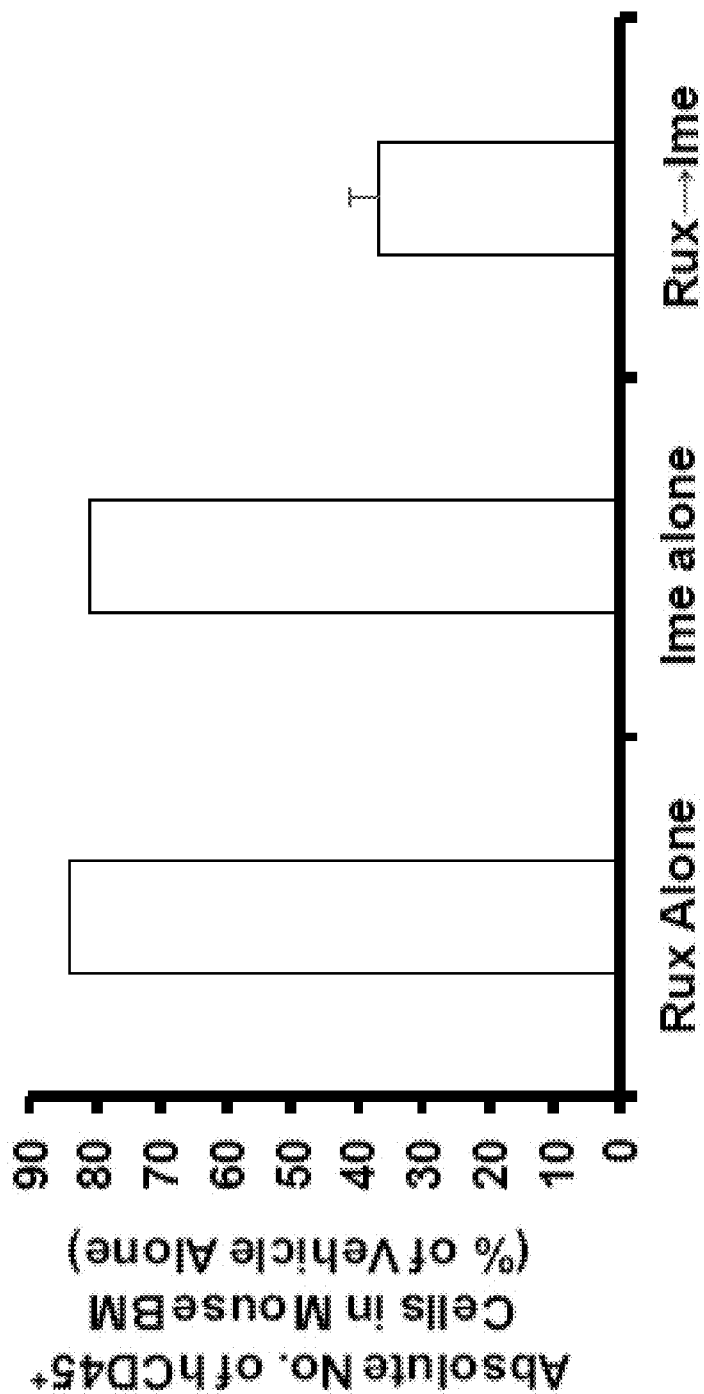

FIG. 11 depicts synergistic activity in depleting myelofibrosis NSG repopulating cells (SRC) with combination treatment in vivo with imetelstat and ruxolitinib according to certain embodiments. NSG mice were transplanted with splenic CD34+ cells of Pt10 and were treated with Rux alone, Ime alone as well as Rux followed by imetelstat due to limited availability of CD34+ cells from this patient. The absolute number of hCD45+ cells detected in marrows of mice receiving drug treatment relative to that generated in mice receiving vehicle alone are shown. Sequential treatment with Rux followed by imetelstat had synergistic activity in depleting MF long-term SRC of Pt10.

Figure 12A:
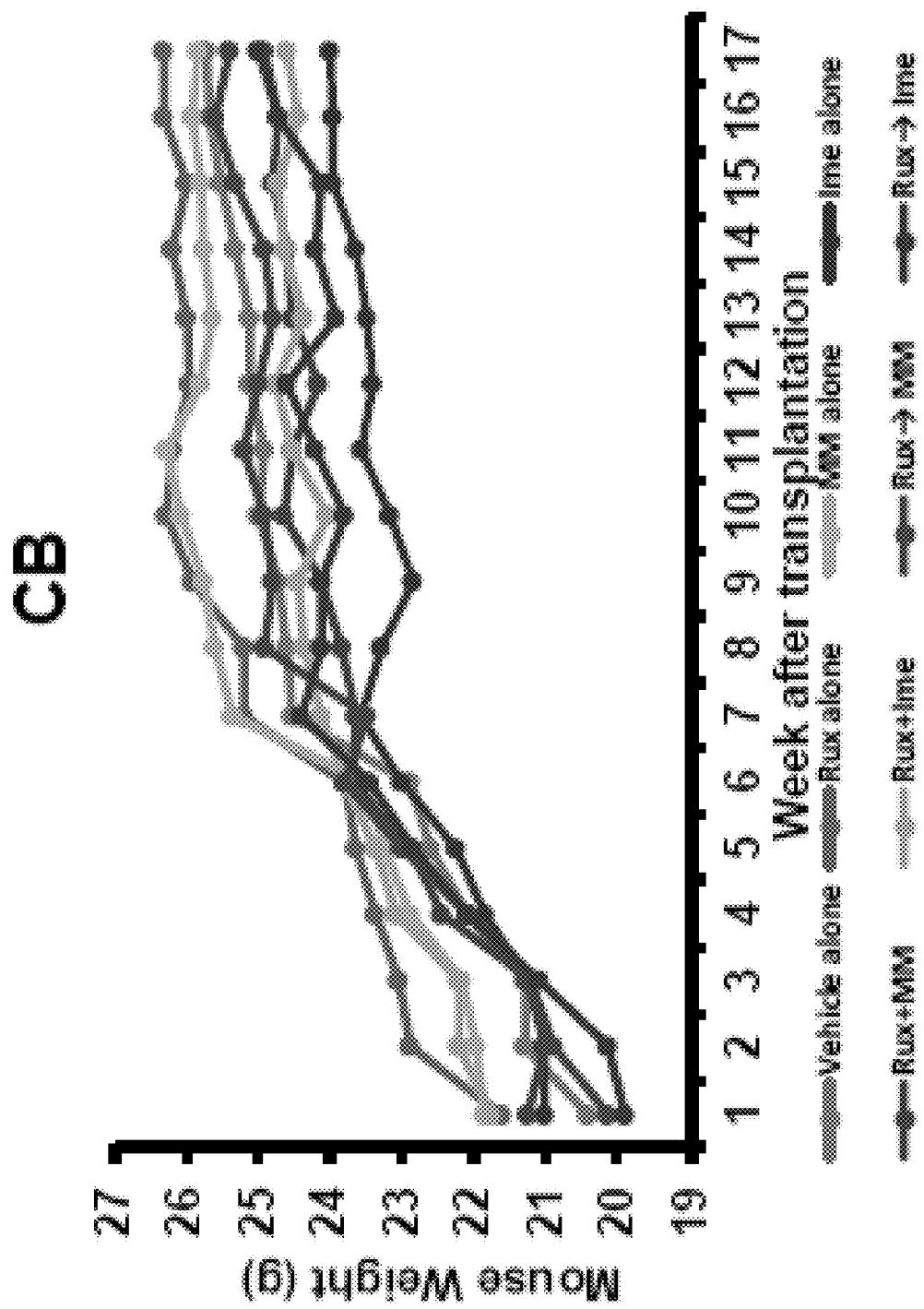
Figure 12B:
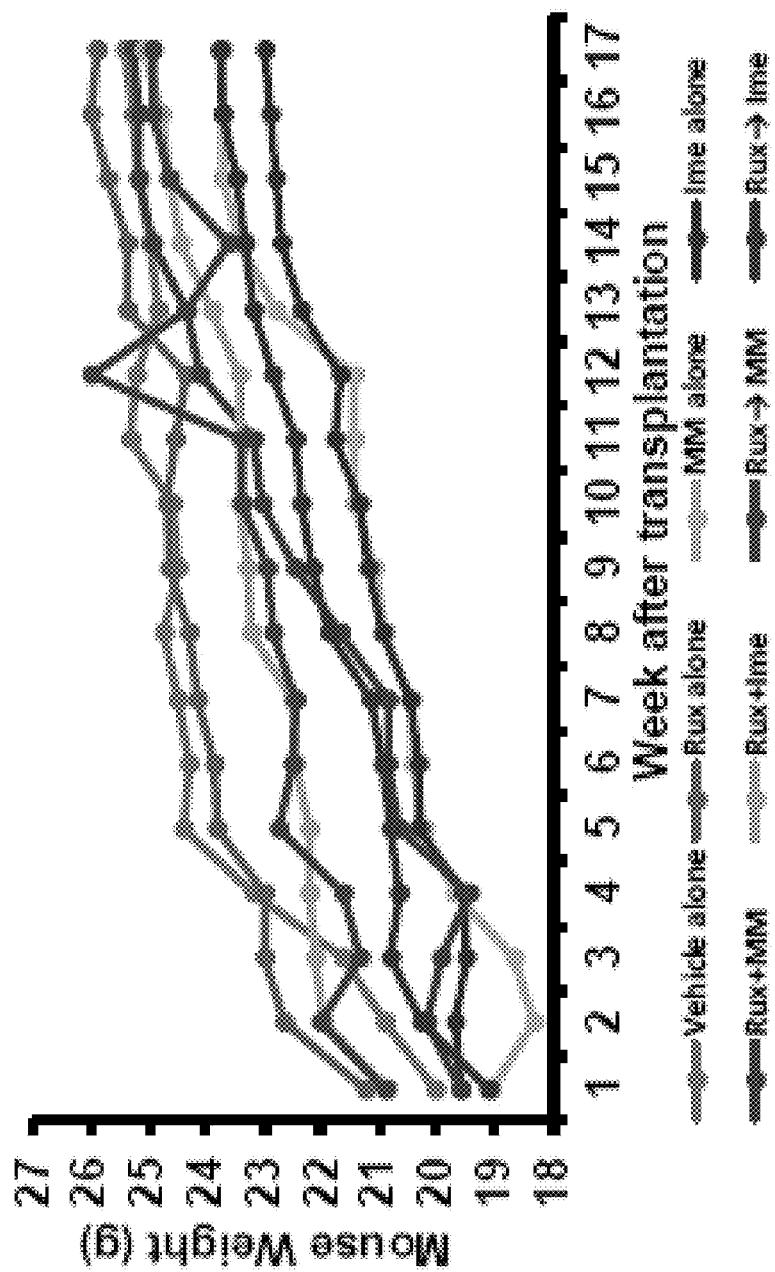

FIGS. 12A and 12B depict a comparison of side effects from in vivo combination treatment of imetelstat and ruxolitinib with imetelstat alone according to certain embodiments. (FIG. 12A, FIG. 12B) NSG mice were transplanted with normal CB (FIG. 12A) or MF (FIG. 12B) splenic CD34$^+$ cells. One week after the transplantation, the mice started being treated with vehicle alone, 45 mg/kg of Rux alone for 7 days or 10 mg/kg of MM or imetelstat alone for 4 weeks or Rux and MM or imetelstat in combination simultaneously or sequentially. The mice were sacrificed 4 months (W17) after the transplantation. Sequential combination treatment of mice receiving either normal CB (FIG. 12A) or MF (FIG. 12B) splenic CD34$^+$ cells did not result in further body weight loss of mice as compared with equal 10 mg/kg dose of imetelstat alone treatment. Moreover, at the time when mice transplanted with MF splenic CD34$^+$ cells (Pt5) were sacrificed, the degree of body weight loss of mice receiving sequential 45 mg/kg of Rux and 10 mg/kg dose of imetelstat (6.5%) was less than equal doses of imetelstat alone (9.6%) or 30 mg/kg dose of imetelstat alone (13.1%). X-axis indicates weeks after the transplantation.

SELECT DEFINITIONS

The term "nucleoside" refers to a moiety having the general structure:

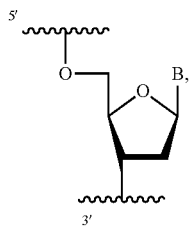

where B represents a nucleobase and the 2' carbon can be substituted as described below. When incorporated into an oligomer or polymer, the 3' carbon is further linked to an oxygen or nitrogen atom. Nucleosides may include 2'-deoxy and 2'-hydroxyl (i.e. deoxyribose and ribose) forms, and analogs thereof. In certain instances, a 5'-NH group can be substituted for the 5'-oxygen. "Analogs", in reference to nucleosides, includes synthetic nucleosides having modified nucleobase moieties (see definition of "nucleobase" below) and/or modified sugar moieties, such as 2'-fluoro sugars, among other analogs. Such analogs are typically designed to affect binding properties, e.g., stability, specificity, or the like. The term nucleoside includes the natural nucleosides, including 2'-deoxy and 2'-hydroxyl forms, e.g., as described in Komberg and Baker, *DNA Replication*, 2nd Ed. (Freeman, San Francisco, 1992), and analogs. "Analogs", in reference to nucleosides, includes synthetic nucleosides having modified nucleobase moieties (see definition of "nucleobase," infra) and/or modified sugar moieties, e.g., described generally by Scheit, *Nucleotide Analogs* (John Wiley, New York, 1980). Such analogs include synthetic nucleosides designed to enhance binding properties, e.g., stability, specificity, or the like, such as disclosed by Uhlmann and Peyman, Chemical Reviews 90:543-584, 1990). An oligonucleotide containing such nucleosides, and which typically contains synthetic nuclease-resistant internucleoside linkages, may itself be referred to as an "analog".

A "polynucleotide" or "oligonucleotide" refers to a ribose and/or deoxyribose nucleoside subunit polymer or oligomer having between about 2 and about 200 contiguous subunits. The nucleoside subunits can be joined by a variety of intersubunit linkages, including, but not limited to, phosphodiester, phosphotriester, methylphosphonate, P3'→N5' phosphoramidate, N3'→P5' phosphoramidate, N3→P5' thiophosphoramidate, and phosphorothioate linkages. The term also includes such polymers or oligomers having modifications, such as to the sugar (e.g., 2' substitutions), the base, and the 3' and 5' termini. In embodiments where the oligonucleotide moiety includes a plurality of intersubunit linkages, each linkage may be formed using the same chemistry, or a mixture of linkage chemistries may be used. When an oligonucleotide is represented by a sequence of letters, such as "ATGUCCTG," it will be understood that the nucleotides are in 5'→3' order from left to right. Representation of the base sequence of the oligonucleotide in this manner does not imply the use of any particular type of internucleoside subunit in the oligonucleotide.

A "nucleobase" includes (i) native DNA and RNA nucleobases (uracil, thymine, adenine, guanine, and cytosine), (ii) modified nucleobases or nucleobase analogs (e.g., 5-methylcytosine, 5-bromouracil, or inosine) and (iii) nucleobase analogs. A nucleobase analog is a compound whose molecular structure mimics that of a typical DNA or RNA base.

The term "lipid" is used broadly herein to encompass substances that are soluble in organic solvents, but sparingly soluble, if at all, in water. The term lipid includes, but is not limited to, hydrocarbons, oils, fats (such as fatty acids and glycerides), sterols, steroids and derivative forms of these compounds. In some embodiments, lipids are fatty acids and their derivatives, hydrocarbons and their derivatives, and sterols, such as cholesterol. Fatty acids usually contain even numbers of carbon atoms in a straight chain (commonly 12-24 carbons) and may be saturated or unsaturated, and can contain, or be modified to contain, a variety of substituent groups. For simplicity, the term "fatty acid" also encompasses fatty acid derivatives, such as fatty or esters. In some embodiments, the term "lipid" also includes amphipathic compounds containing both lipid and hydrophilic moieties.

An "individual" or a "patient" or a "subject" can be a mammal, such as any common laboratory model organism. Mammals include, but are not limited to, humans and non-human primates, farm animals, sport animals, pets, mice, rats, and other rodents. In some embodiments, an individual or patient or subject is a human. In certain embodiments, the subject or patient has not previously received JAK-inhibitor therapy and/or telomerase inhibitor therapy prior to certain embodiments, such patients are "JAK inhibitor naïve" or "telomerase inhibitor naïve" respectively.

An "effective amount" or "therapeutically effective amount" or "clinically effective amount" refers to an amount of therapeutic compound, such as a JAK inhibitor or telomerase inhibitor, administered to a mammalian subject, either as a single dose or as part of a series of doses, which is effective to produce a desired therapeutic effect. One advantage of the present invention is that the telomerase inhibitor, when administered in combination with the JAK inhibitor, may be administered at doses lower than single-agent doses, thus reducing side effects and the overall toxicity of the compound, while achieving comparable or superior treatment effects. In certain embodiments, when a telomerase inhibitor is co-administered with a JAK inhibitor according to embodiments described herein, the amount of JAK inhibitor that is needed to achieve a therapeutically effective response may be reduced by 1% or more by weight, such as by 2% or more by weight, such as by 3% or more by weight, such as by 5% or more by weight, such as by 10% or more by weight, such as by 15% or more by weight, such as by 25% or more by weight and including reducing the amount JAK inhibitor needed to achieve a therapeutically effective response by 50% or more by weight. In other words, the amount of JAK inhibitor needed to achieve a therapeutically effective response is reduced by 1% or more by weight as compared to the amount of JAK inhibitor alone that is needed to achieve a therapeutically effective response. In other embodiments, when a JAK inhibitor is co-administered with a telomerase inhibitor according to embodiments described herein, the amount of telomerase inhibitor that is needed to achieve a therapeutically effective response may be reduced by 1% or more by weight, such as by 2% or more by weight, such as by 3% or more by weight, such as by 5% or more by weight, such as by 10% or more by weight, such as by 15% or more by weight, such as by 25% or more by weight and including reducing the amount telomerase inhibitor needed to achieve a therapeutically effective response by 50% or more by weight. In other words, the amount of telomerase inhibitor needed to achieve a therapeutically effective response is reduced by 1% or more by weight as compared to the amount of telomerase inhibitor alone that is needed to achieve a therapeutically effective response, such as by 2% or more by weight, such as by 3% or more by weight, such as by 5% or more by weight, such as by 10% or more by weight, such as by 15% or more by weight, such as by 25% or more and including by 50% or more by weight.

As used herein, "neoplastic cells" refer to cells which exhibit relatively autonomous growth, so that they exhibit an aberrant growth phenotype characterized by a significant loss of control of cell proliferation. Neoplastic cells comprise cells which may be actively replicating or in a temporary non-replicative resting state (Gi or Go); similarly, neoplastic cells may comprise cells which have a well-differentiated phenotype, a poorly-differentiated phenotype, or a mixture of both type of cells. Thus, not all neoplastic cells are necessarily replicating cells at a given timepoint. "Neoplastic cells" encompass such cells in benign neoplasms and cells in malignant neoplasms.

As used herein, "neoplastic progenitor cells" refers to cells of a cellular composition that possess the ability to become neoplastic.

As used herein, the term "neoplasm" or "neoplasia" or "neoplastic" refers to abnormal new cell growth. Unlike hyperplasia, neoplastic proliferation persists even in the absence of an original stimulus.

As used herein, the singular form "a", "an", and "the" includes plural references unless indicated otherwise.

It is intended that every maximum numerical limitation given throughout this specification includes every lower numerical limitation, as if such lower numerical limitations were expressly written herein. Every minimum numerical limitation given throughout this specification will include every higher numerical limitation, as if such higher numerical limitations were expressly written herein. Every numerical range given throughout this specification will include every narrower numerical range that falls within such broader numerical range, as if such narrower numerical ranges were all expressly written herein.

Before the present invention is further described, it is to be understood that this invention is not limited to particular embodiments described, as such may, of course, vary. It is also to be understood that the terminology used herein is for the purpose of describing particular embodiments only, and is not intended to be limiting, since the scope of the present invention will be limited only by the appended claims.

Where a range of values is provided, it is understood that each intervening value, to the tenth of the unit of the lower limit unless the context clearly dictates otherwise, between the upper and lower limit of that range and any other stated or intervening value in that stated range, is encompassed within the invention. The upper and lower limits of these smaller ranges may independently be included in the smaller ranges, and are also encompassed within the invention, subject to any specifically excluded limit in the stated range. Where the stated range includes one or both of the limits, ranges excluding either or both of those included limits are also included in the invention.

It is appreciated that certain features of the invention, which are, for clarity, described in the context of separate embodiments, may also be provided in combination in a single embodiment. Conversely, various features of the invention, which are, for brevity, described in the context of a single embodiment, may also be provided separately or in any suitable sub-combination. All combinations of the embodiments pertaining to the invention are specifically embraced by the present invention and are disclosed herein just as if each and every combination was individually and explicitly disclosed, to the extent that such combinations embrace subject matter that are, for example, compounds that are stable compounds (i.e., compounds that can be made, isolated, characterized, and tested for biological activity). In addition, all sub-combinations of the various embodiments and elements thereof (e.g., elements of the chemical groups listed in the embodiments describing such variables) are also specifically embraced by the present invention and are disclosed herein just as if each and every such sub-combination was individually and explicitly disclosed herein.

Unless defined otherwise, all technical and scientific terms used herein have the same meaning as commonly understood by one of ordinary skill in the art to which this invention belongs. Although any methods and materials similar or equivalent to those described herein can also be used in the practice or testing of the present invention, methods and materials of interest are now described. All publications mentioned herein are incorporated herein by reference to disclose and describe the methods and/or materials in connection with which the publications are cited.

It must be noted that as used herein and in the appended claims, the singular forms "a," "an," and "the" include plural referents unless the context clearly dictates otherwise. It is further noted that the claims may be drafted to exclude any optional element. As such, this statement is intended to serve as antecedent basis for use of such exclusive terminology as "solely," "only" and the like in connection with the recitation of claim elements, or use of a "negative" limitation.

It is appreciated that certain features of the invention, which are, for clarity, described in the context of separate embodiments, may also be provided in combination in a single embodiment. Conversely, various features of the invention, which are, for brevity, described in the context of a single embodiment, may also be provided separately or in any suitable sub-combination.

The publications discussed herein are provided solely for their disclosure prior to the filing date of the present application. Nothing herein is to be construed as an admission that the present invention is not entitled to antedate such publication by virtue of prior invention. Further, the dates of publication provided may be different from the actual publication dates which may need to be independently confirmed.

Compounds as described herein can be purified by any of the means known in the art, including chromatographic means, such as high performance liquid chromatography (HPLC), preparative thin layer chromatography, flash column chromatography and ion exchange chromatography. Any suitable stationary phase can be used, including normal and reversed phases as well as ionic resins. See, e.g., Introduction to Modern Liquid Chromatography, 2nd Edition, ed. L. R. Snyder and J. J. Kirkland, John Wiley and Sons, 1979; and Thin Layer Chromatography, ed E. Stahl, Springer-Verlag, New York, 1969.

The compounds described herein can contain one or more chiral centers and/or double bonds and therefore, can exist as stereoisomers, such as double-bond isomers (i.e., geometric isomers), enantiomers or diastereomers. Accordingly, all possible enantiomers and stereoisomers of the compounds including the stereoisomerically pure form (e.g., geometrically pure, enantiomerically pure or diastereomerically pure) and enantiomeric and stereoisomeric mixtures are included in the description of the compounds herein. Enantiomeric and stereoisomeric mixtures can be resolved into their component enantiomers or stereoisomers using separation techniques or chiral synthesis techniques well known to the skilled artisan. The compounds can also exist in several tautomeric forms including the enol form, the keto form and mixtures thereof. Accordingly, the chemical structures depicted herein encompass all possible tautomeric forms of the illustrated compounds. The compounds described also include isotopically labeled compounds where one or more atoms have an atomic mass different from the atomic mass conventionally found in nature. Examples of isotopes that can be incorporated into the compounds disclosed herein include, but are not limited to, $^2H$, $^3H$, $^{11}C$, $^{13}C$, $^{14}C$, $^{15}N$, $^{18}O$, $^{17}O$, etc. Compounds can exist in unsolvated forms as well as solvated forms, including hydrated forms. In general, compounds can be hydrated or solvated. Certain compounds can exist in multiple crystalline or amorphous forms. In general, all physical forms are equivalent for the uses contemplated herein and are intended to be within the scope of the present disclosure.

DETAILED DESCRIPTION

Aspects of the disclosure include methods for treating a myeloproliferative neoplasm. Methods according to certain embodiments include co-administering to a subject a Janus kinase (JAK) inhibitor and a telomerase inhibitor comprising an oligonucleotide and a lipid moiety linked to the 5' and/or 3' end of the oligonucleotide. In some instances, treating a myeloproliferative neoplasm includes inducing apoptosis of a myeloproliferative neoplasm cell, such as inducing apoptosis of a myeloproliferative neoplasm cell in vitro. In other instances, treating a myeloproliferative neoplasm includes inducing apoptosis of a myeloproliferative neoplasm cell in a subject. In some embodiments, the myeloproliferative neoplasm cell is a malignant hematopoietic stem cell (HSC). In other embodiments, the myeloproliferative neoplasm cell is a malignant hematopoietic progenitor cell (HPC). Myeloproliferative neoplasms treated according to the subject methods may include, for example myelofibrosis (MF), such as primary myelofibrosis, or myelofibrosis following previous ET or PV (post-ETMF or post-PVMF). In other embodiments, the myeloproliferative neoplasm includes Essential Thrombocythemia (ET), Polycythemia vera (PV), Chronic Myelogenous Leukemia (CML), chronic neutrophilic leukemia, chronic eosinophilic leukemia and acute myelogenous leukemia (AML). In other embodiments, the myeloproliferative neoplasm is myelodysplastic syndromes (MDS). In still other embodiments, the myeloproliferative neoplasm is myelodysplastic syndromes (MDS) with isolated del (5q). Myelodysplastic syndromes (MDS) includes diseases such as, refractory anemia, refractory anemia with excess blasts, refractory cytopenia with multilineage dysplasia, refractory cytopenia with unilineage dysplasia, and chronic myelomonocytic leukemia (CMML).

In some embodiments, co-administering the JAK inhibitor and the telomerase inhibitor includes simultaneously administering the JAK inhibitor and the telomerase inhibitor. In some instances where the JAK inhibitor and the telomerase inhibitor are administered simultaneously, the JAK inhibitor and the telomerase inhibitor are co-formulated (e.g., combined into a single dosage form such as a tablet, injectable, lyophilate, intravenous fluid, etc.) and administered to the subject as a single dose. In other instances where the JAK inhibitor and the telomerase inhibitor are administered simultaneously, the JAK inhibitor and the telomerase inhibitor are formulated as two distinct compositions and are administered to the subject at the same time.

In other embodiments, co-administering the JAK inhibitor and the telomerase inhibitor includes sequentially administering the JAK inhibitor and the telomerase inhibitor In some embodiments, the JAK inhibitor is administered first to the subject followed by administration of the telomerase inhibitor to the subject. In one example, the telomerase inhibitor is administered to the subject on the same day as the JAK inhibitor is administered to the subject. In another example, the telomerase inhibitor is administered to the subject within 13 days after the JAK inhibitor is administered to the subject. For instance, the telomerase inhibitor is administered within three days after the last dosage of the JAK inhibitor is administered to the subject.

In embodiments, the telomerase inhibitor may be administered to the subject within about 14 days after administering the JAK inhibitor, such as administering the telomerase inhibitor to the subject from about 0 days to about 13 days after administering the JAK inhibitor, such as from about 1 day to about 12 days, such as from about 2 days to about 11 days, such as from about 3 days to about 10 days, such as from about 4 days to about 9 days, such as from about 5 days to about 8 days and including administering the telomerase inhibitor to the subject from about 6 days to about 7 days after administering the JAK inhibitor. In some embodiments, the telomerase inhibitor is administered within 3 days after the JAK inhibitor is administered. In certain instances, the JAK inhibitor is administered to the subject for a predetermined duration (e.g., for a duration of from 0 days to 7 days, as described in greater detail below) and the telomerase inhibitor is administered to the subject within about 14 days after the last dose of the JAK inhibitor, such as administering the telomerase inhibitor to the subject from about 0 days to about 13 days after the last dose of the JAK inhibitor, such as from about 1 day to about 12 days, such as from about 2 days to about 11 days, such as from about 3 days to about 10 days, such as from about 4 days to about 9 days, such as from about 5 days to about 8 days and including administering the telomerase inhibitor to the subject from about 6 days to about 7 days after the last dose of the JAK inhibitor.

In some instances, the telomerase inhibitor is administered within 3 days after the last dose of the JAK inhibitor.

In some embodiments, the telomerase inhibitor is administered first to the subject followed by administration of the JAK inhibitor to the subject. In some instances, the JAK inhibitor is administered to the subject within 13 days after the telomerase inhibitor is administered to the subject. For instance, the JAK inhibitor is administered within three days after the last dosage of the telomerase inhibitor is administered to the subject and twice daily thereafter.

The dosing is administered in cycles of administration of a JAK inhibitor and a telomerase inhibitor. In some embodiments, the cycle is 21 days, in some instances the cycle is 28 or more days. The cycles of drug administration may be repeated for 1, 2, 3, 4, 5, 6, 7, 8 or more than 8 dosage cycles, for a total period of 6 months or 1 year or 2 years or 3 years or 4 years or more.

In certain embodiments, treating a myeloproliferative neoplasm includes treating a subject with a 21-day administrative cycle of a JAK inhibitor or a pharmaceutically acceptable salt thereof and a telomerase inhibitor or a pharmaceutically acceptable salt thereof where methods include administering the JAK inhibitor once or twice per day for 21 days and administering the telomerase inhibitor to the subject on the first day of the 21-day administration cycle. (i.e., the JAK inhibitor or a pharmaceutically acceptable salt thereof and telomerase inhibitor or pharmaceutically acceptable salt thereof are both administered to the subject on first day of the 21-day cycle). In certain instances, methods include a 21-day administration cycle of the JAK inhibitor or pharmaceutically acceptable salt thereof and telomerase inhibitor or a pharmaceutically acceptable salt thereof where the JAK inhibitor is administered once per day for 21 days and the telomerase inhibitor is administered on the first day of the 21-day cycle. In other instances, methods include a 21-day administration cycle of the JAK inhibitor or pharmaceutically acceptable salt thereof and the telomerase inhibitor or pharmaceutically acceptable salt thereof where the JAK inhibitor is administered twice per day for 21 days and the telomerase inhibitor is administered on the first day of the 21-day cycle. The 21-day administration cycle of administering the JAK inhibitor or pharmaceutically acceptable salt thereof and the telomerase inhibitor or pharmaceutically acceptable salt thereof according to these embodiments can be repeated 1 or more times, such as 2 or more times, such as 3 or more times, such as 4 or more times, such as 5 or more times, such as 6 or more time, such as 7 or more times, such as 8 or more times, such as 9 or more times and including 10 or more times. Where the 21-day administration cycle of the JAK inhibitor and the telomerase inhibitor is repeated 1 or more times, the duration between each 21-day administration cycle may be 0 days or more, such as 1 day or more, such as 2 days or more, such as 3 days or more, such as 4 days or more, such as 5 days or more, such as 6 days or more and including 7 days or more. Depending on the number of 21-day administration cycles of the JAK inhibitor and the telomerase inhibitor employed and the duration between each cycle, the duration of treatment of the subject according to these embodiments may be about 1.5 months or more, such as 3 months or more, such as 6 months or more, such as 1 year or more, such as 2 years or more, such as 3 years or more, such as 4 years or more, such as 5 years or more, such as 6 years or more, such as 7 years or more, such as 8 years or more, such as 9 years or more and including for 10 years or more.

In certain embodiments, treating a myeloproliferative neoplasm includes treating a subject with a 28-day administrative cycle of a JAK inhibitor or a pharmaceutically acceptable salt thereof and a telomerase inhibitor or a pharmaceutically acceptable salt thereof where methods include administering the JAK inhibitor once or twice per day for 28 days and administering the telomerase inhibitor to the subject on the first day of the 28-day administration cycle. (i.e., the JAK inhibitor or a pharmaceutically acceptable salt thereof and telomerase inhibitor or pharmaceutically acceptable salt thereof are both administered to the subject on first day of the 28-day cycle). In certain instances, methods include a 28-day administration cycle of the JAK inhibitor or pharmaceutically acceptable salt thereof and telomerase inhibitor or a pharmaceutically acceptable salt thereof where the JAK inhibitor is administered once per day for 28 days and the telomerase inhibitor is administered on the first day of the 28-day cycle. In other instances, methods include a 28-day administration cycle of the JAK inhibitor or pharmaceutically acceptable salt thereof and the telomerase inhibitor or pharmaceutically acceptable salt thereof where the JAK inhibitor is administered twice per day for 28 days and the telomerase inhibitor is administered on the first day of the 28-day cycle. The 28-day administration cycle of administering the JAK inhibitor or pharmaceutically acceptable salt thereof and the telomerase inhibitor or pharmaceutically acceptable salt thereof according to these embodiments can be repeated 1 or more times, such as 2 or more times, such as 3 or more times, such as 4 or more times, such as 5 or more times, such as 6 or more time, such as 7 or more times, such as 8 or more times, such as 9 or more times and including 10 or more times. Where the 28-day administration cycle of the JAK inhibitor and the telomerase inhibitor is repeated 1 or more times, the duration between each 28-day administration cycle may be 0 days or more, such as 1 day or more, such as 2 days or more, such as 3 days or more, such as 4 days or more, such as 5 days or more, such as 6 days or more and including 7 days or more. Depending on the number of 28-day administration cycles of the JAK inhibitor and the telomerase inhibitor employed and the duration between each cycle, the duration of treatment of the subject according to these embodiments may be about 2 months or more, such as 4 months or more, such as 6 months or more, such as 1 year or more, such as 2 years or more, such as 3 years or more, such as 4 years or more, such as 5 years or more, such as 6 years or more, such as 7 years or more, such as 8 years or more, such as 9 years or more and including for 10 years or more.

In certain embodiments, treating a myeloproliferative neoplasm includes treating a subject with an administration cycle of a JAK inhibitor or a pharmaceutically acceptable salt thereof and a telomerase inhibitor or a pharmaceutically acceptable salt thereof where the JAK inhibitor or pharmaceutically acceptable salt thereof is administered to the subject once or twice per day for 14 days or 21 days followed by administering one or more doses of a telomerase inhibitor or pharmaceutically acceptable salt thereof to the subject during the period from 1 day to 7 days after the last administered dosage of the JAK inhibitor or pharmaceutically acceptable salt thereof for that administration cycle. In one example, methods include an administration cycle where the JAK inhibitor or pharmaceutically acceptable salt thereof is administered to the subject once per day for 14 days followed by administering one or more doses of a telomerase inhibitor or pharmaceutically acceptable salt thereof during the period from 1 day to 7 days after the last administered dosage of the JAK inhibitor or pharmaceutically acceptable salt thereof. In another example, methods include an administration cycle where the JAK inhibitor or pharmaceutically acceptable salt thereof is administered to the subject once per day for 21 days followed by administering one or more doses of a telomerase inhibitor or pharmaceutically acceptable salt thereof during the period from 1 day to 7 days after the last administered dosage of the JAK inhibitor or pharmaceutically acceptable salt thereof. In yet another example, methods include an administration cycle where the JAK inhibitor or pharmaceutically acceptable salt thereof is administered to the subject twice per day for 14 days followed by administering one or more doses of a telomerase inhibitor or pharmaceutically acceptable salt thereof during the period from 1 day to 7 days after the last administered dosage of the JAK inhibitor or pharmaceutically acceptable salt thereof. In still another example, methods include an administration cycle where the JAK inhibitor or pharmaceutically acceptable salt thereof is administered to the subject twice per day for 21 days followed by administering one or more doses of the telomerase inhibitor or pharmaceutically acceptable salt thereof during the period from 1 day to 7 days after the last administered dosage of the JAK inhibitor or pharmaceutically acceptable salt thereof. In these embodiments, one or more doses of the telomerase inhibitor or pharmaceutically acceptable salt thereof is administered to the subject from 1 day to 7 days after the last administered dosage of JAK inhibitor or pharmaceutically acceptable salt thereof, such as 1 day after, such as 2 days after, such as 3 days after, such as 4 days after, such as 5 days after, such as 6 days after and including administering the telomerase inhibitor or pharmaceutically acceptable salt thereof 7 days after the last administered dosage of the JAK inhibitor or pharmaceutically acceptable salt thereof. The administration cycle of the JAK inhibitor or a pharmaceutically acceptable salt thereof and the telomerase inhibitor or a pharmaceutically acceptable salt thereof according to these embodiments can be repeated 1 or more times, such as 2 or more times, such as 3 or more times, such as 4 or more times, such as 5 or more times, such as 6 or more time, such as 7 or more times, such as 8 or more times, such as 9 or more times and including 10 or more times.

In certain embodiments, treating a myeloproliferative neoplasm includes treating a subject with a 21-day administrative cycle of a telomerase inhibitor or a pharmaceutically acceptable salt thereof and a JAK inhibitor or a pharmaceutically acceptable salt thereof where methods include administering the telomerase inhibitor or a pharmaceutically acceptable salt thereof to the subject on the first day of the 21-day administration cycle followed by administering the JAK inhibitor or a pharmaceutically acceptable salt thereof to the subject once or twice per day on each subsequent day of the 21-day cycle (i.e., the telomerase inhibitor or pharmaceutically acceptable salt thereof is administered to the subject on first day of the 21-day cycle and the JAK inhibitor or a pharmaceutically acceptable salt thereof is administered once or twice per day on days 2-21 of the 21-day administration cycle). In certain instances, methods include administering the telomerase inhibitor or a pharmaceutically acceptable salt thereof to the subject on the first day of the 21-day administration cycle followed by administering the JAK inhibitor or a pharmaceutically acceptable salt thereof to the subject once per day on each subsequent day of the 21-day cycle. In other instances, methods include administering the telomerase inhibitor or a pharmaceutically acceptable salt thereof to the subject on the first day of the 21-day administration cycle followed by administering the JAK inhibitor or a pharmaceutically acceptable salt thereof to the subject twice per day on each subsequent day of the 21-day cycle. In the 21 day cycle, the administration of the JAK inhibitor or a pharmaceutically acceptable salt thereof may be delayed for 1, 2, 3, 4, 5, 6, 7, 8, 9, 10, 11, 12, 13 day(s) before administration either once or twice a day. The 21-day administration cycle of administering the telomerase or a pharmaceutically acceptable salt thereof followed by the JAK inhibitor or a pharmaceutically acceptable salt thereof according to these embodiments can be repeated 1 or more times, such as 2 or more times, such as 3 or more times, such as 4 or more times, such as 5 or more times, such as 6 or more time, such as 7 or more times, such as 8 or more times, such as 9 or more times and including 10 or more times. Where the 21-day administration cycle of telomerase inhibitor and JAK inhibitor is repeated 1 or more times, the duration between each 21-day administration cycle may be 0 days or more, such as 1 day or more, such as 2 days or more, such as 3 days or more, such as 4 days or more, such as 5 days or more, such as 6 days or more and including 7 days or more. Depending on the number of 21-day administration cycles of the telomerase inhibitor and the JAK inhibitor employed and the duration between each cycle, the duration of treatment of the subject according to these embodiments may be about 1.5 months or more, such as 3 months or more, such as 6 months or more, such as 1 year or more, such as 2 years or more, such as 3 years or more, such as 4 years or more, such as 5 years or more, such as 6 years or more, such as 7 years or more, such as 8 years or more, such as 9 years or more and including for 10 years or more.

In certain embodiments, treating a myeloproliferative neoplasm includes treating a subject with a 28-day administrative cycle of a telomerase inhibitor or a pharmaceutically acceptable salt thereof and a JAK inhibitor or a pharmaceutically acceptable salt thereof where methods include administering the telomerase inhibitor or a pharmaceutically acceptable salt thereof to the subject on the first day of the 28-day administration cycle followed by administering the JAK inhibitor or a pharmaceutically acceptable salt thereof to the subject once or twice per day on each subsequent day of the 28-day cycle (i.e., the telomerase inhibitor or pharmaceutically acceptable salt thereof is administered to the subject on first day of the 28-day cycle and the JAK inhibitor or a pharmaceutically acceptable salt thereof is administered once or twice per day on days 2-28 of the 28-day administration cycle). In certain instances, methods include administering the telomerase inhibitor or a pharmaceutically acceptable salt thereof to the subject on the first day of the 28-day administration cycle followed by administering the JAK inhibitor or a pharmaceutically acceptable salt thereof to the subject once per day on each subsequent day of the 28-day cycle. In other instances, methods include administering the telomerase inhibitor or a pharmaceutically acceptable salt thereof to the subject on the first day of the 28-day administration cycle followed by administering the JAK inhibitor or a pharmaceutically acceptable salt thereof to the subject twice per day on each subsequent day of the 28-day cycle. In the 28 day cycle, the administration of the JAK inhibitor or a pharmaceutically acceptable salt thereof may be delayed for 1, 2, 3, 4, 5, 6, 7, 8, 9, 10, 11, 12, 13 day(s) before administration either once or twice a day. The 28-day administration cycle of administering the telomerase or a pharmaceutically acceptable salt thereof followed by the JAK inhibitor or a pharmaceutically acceptable salt thereof according to these embodiments can be repeated 1 or more times, such as 2 or more times, such as 3 or more times, such as 4 or more times, such as 5 or more times, such as 6 or more time, such as 7 or more times, such as 8 or more times, such as 9 or more times and including 10 or more times. Where the 28-day administration cycle of telomerase inhibitor and JAK inhibitor is repeated 1 or more times, the duration between each 28-day administration cycle may be 0 days or more, such as 1 day or more, such as 2 days or more, such as 3 days or more, such as 4 days or more, such as 5 days or more, such as 6 days or more and including 7 days or more. Depending on the number of 28-day administration cycles of the telomerase inhibitor and the JAK inhibitor employed and the duration between each cycle, the duration of treatment of the subject according to these embodiments may be about 2 months or more, such as 4 months or more, such as 6 months or more, such as 1 year or more, such as 2 years or more, such as 3 years or more, such as 4 years or more, such as 5 years or more, such as 6 years or more, such as 7 years or more, such as 8 years or more, such as 9 years or more and including for 10 years or more.

In other embodiments, methods include administering JAK inhibitor or a pharmaceutically acceptable salt thereof for a predetermined duration (from 1 days to 21 days), discontinuing administration of the JAK inhibitor or pharmaceutically acceptable salt thereof and administering a telomerase inhibitor or pharmaceutically acceptable salt thereof within 7 days (e.g., 2 days, 1 day or on the same day) of the last dosage of JAK inhibitor or pharmaceutically acceptable salt thereof administered to the subject. This administration cycle may be repeated, such as 2 or more times, such as 3 or more times, such as 4 or more times, such as 5 or more times, such as 6 or more time, such as 7 or more times, such as 8 or more times, such as 9 or more times and including 10 or more times.

The term Janus kinase (JAK) inhibitor as used herein refers to compounds which inhibit the activity of one or more Janus kinase enzymes, such as Janus kinase 1 (JAK1), Janus kinase 2 (JAK2), Janus kinase 3 (JAK3) and tyrosine kinase 2 (TYK2). In certain embodiments, JAK inhibitors of interest interfere with the Janus kinase/signal transducers and activators of transcription (JAK-STAT) pathway. Examples of JAK inhibitors include, but are not limited to, ruxolitinib ((3R)-3-Cyclopentyl-3-[4-(7H-pyrrolo[2,3-d]pyrimidin-4-yl)pyrazol-1-yl]propanenitrile), Tofacitinib (3-[(3R,4R)-4-Methyl-3-[methyl(7H-pyrrolo[2,3-d]pyrimidin-4-yl)amino]piperidin-1-yl]-3-oxopropanenitrile), Oclacitinib (N-Methyl{trans-4-[methyl(7H-pyrrolo[2,3-d]pyrimidin-4-yl)amino]cyclohexyl}methanesulfonamide), Baricitinib (2-[1-Ethylsulfonyl-3-[4-(7H-pyrrolo[2,3-d]pyrimidin-4-yl)pyrazol-1-yl]azetidin-3-yl]acetonitrile), Peficitinib (4-[[(1R,3S)-5-hydroxy-2-adamantyl]amino]-1H-pyrrolo[2,3-b]pyridine-5-carboxamide), Fedratinib (N-tert-Butyl-3-{5-methyl-2-[4-(2-pyrrolidin-1-yl-ethoxy)-phenylamino]-pyrimidin-4-ylamino}-benzenesulfonamide), Upadacitinib ((3S,4R)-3-Ethyl-4-(3H-imidazo[1,2-a]pyrrolo[2,3-e]pyrazin-8-yl)-N-(2,2,2-trifluoroethyl)pyrrolidine-1-carboxamide), Filgotinib (N-[5-[4-[(1,1-Dioxo-1,4-thiazinan-4-yl)methyl]phenyl]-[1,2,4]triazolo[1,5-a]pyridin-2-yl]cyclopropanecarboxamide), Cerdulatinib (4-(Cyclopropylamino)-2-[4-(4-ethylsulfonylpiperazin-1-yl)anilino]pyrimidine-5-carboxamide), Gandotinib (3-(4-Chloro-2-fluorobenzyl)-2-methyl-N-(5-methyl-1H-pyrazol-3-yl)-8-(morpholinomethyl)imidazo[1,2-b]pyridazin-6-amine), Lestaurtinib ((5S,6S,8R)-6-Hydroxy-6-(hydroxymethyl)-5-methyl-7,8,14,15-tetrahydro-5H-16-oxa-4b,8a,14-triaza-5,8-methanodibenzo[b,h]cycloocta[jkl]cyclopenta[e]-as-indacen-13(6H)-one), Momelotinib (N-(cyanomethyl)-4-{2-[4-(morpholin-4-yl)anilino]pyrimidin-4-yl}benzamide) and Pacritinib ((16E)-11-[2-(1-Pyrrolidinyl)ethoxy]-14,19-dioxa-5,7,26-triazatetracyclo [19.3.1.12,6.18,12]heptacosa-1(25),2(26),3,5,8,10,12(27),16,21,23-decaene) and pharmaceutically acceptable salts thereof. In certain embodiments, the JAK inhibitor is selected from the group consisting of ruxolitinib, fedratinib, momelotinib and pacritinib or pharmaceutically acceptable salts thereof and combinations thereof. In certain embodiments, the JAK inhibitor is ruxolitinib or pharmaceutically acceptable salt thereof. In certain embodiments, the JAK inhibitor is fedratinib or pharmaceutically acceptable salt thereof. In certain embodiments, the JAK inhibitor is momelotinib or pharmaceutically acceptable salt thereof. In certain embodiments, the JAK inhibitor is pacritinib or pharmaceutically acceptable salt thereof.

In embodiments, the term telomerase inhibitor as used herein refers to a compound which is capable of reducing or inhibiting the activity of telomerase reverse transcriptase enzyme in a mammalian cell. Telomerase inhibitors of interest, in some instances, include a hTR template inhibitor including an oligonucleotide. An "hTR template inhibitor" is a compound that blocks the template region of the RNA component of human telomerase and can inhibit the activity of the enzyme. In some embodiments, the oligonucleotide includes a sequence effective to hybridize to a more specific portion of this region, having sequence 5'-CUAACCC-UAAC-3' (SEQ ID NO: 23).

Telomerase inhibitors of interest include an oligonucleotide and a lipid moiety linked to the 5' and/or 3' end of the oligonucleotide. In some embodiments, the telomerase inhibitor includes an oligonucleotide having "nuclease-resistant linkages" having a backbone with subunit linkages that are substantially resistant to nuclease cleavage, in non-hybridized or hybridized form, by extracellular and intracellular nucleases. In some instances, the oligonucleotide shows little or no nuclease cleavage under physiological conditions.

The region of the therapeutic oligonucleotide that is targeted to the hTR sequence is, in some embodiments, complementary to the corresponding hTR sequence. In certain embodiments, the base sequence of the oligonucleotide includes a sequence of 5 nucleotides or more that are complementary to the hTR target, such as 8 nucleotides or more, such as 10 nucleotides or more, such as 12 nucleotides or more, such as 15 nucleotides or more that are complementary to the hTR target. In certain embodiments, oligonucleotides in telomerase inhibitors of the present disclosure are fully complimentary to the hTR target sequence, such as where the full length of the oligonucleotide is complementary to the hTR target sequence.

The telomerase inhibitor includes internucleoside linkages, such as phosphodiester, phosphotriester, methylphosphonate, P3'→N5' phosphoramidate, N3'→P5' phosphoramidate, N3'→P5' thiophosphoramidate, and phosphorothioate linkages. In certain embodiments, telomerase inhibitors of interest include at least one N3'→P5' phosphoramidate (NP) or N3'→P5' thiophosphoramidate (NPS) linkage, which linkage may be represented by the structure: 3'-(—NH—P(=O)(—XR)—O—)-5', wherein X is O or S and R is selected from the group consisting of hydrogen, alkyl, and aryl; and pharmaceutically acceptable salts thereof, when XR is OH or SH. In other embodiments, the oligonucleotide includes all NP or, in some embodiments, all NPS linkages. In one embodiment, the sequence for an hTR template inhibitor oligonucleotide is the sequence complementary to nucleotides 42-54 of

SEQ ID NO: 1
(GGGUUGCGGAGGGUGGGCCUGGGAGGGGUGGUGGCCAUUU

UUUGUCUAACCCUAACUGAGAAGGGCGUAGGCGCCGUGCUUUUGCUCCCC

GCGCGCUGUUUUUCUCGCUGACUUUCAGCGGGCGGAAAAGCCUCGGCCUG

CCGCCUUCCACCGUUCAUUCUAGAGCAAACAAAAAAUGUCAGCUGCUGGC

CCGUUCGCCUCCCGGGGACCUGCGGCGGGUCGCCUGCCCAGCCCCGAAC

CCCGCCUGGAGCCGCGGUCGGCCCGGGGCUUCUCCGGAGGCACCCACUGC

CACCGCGAAGAGUUGGGCUCUGUCAGCCGCGGGUCUCUCGGGGGCGAGGG

CGAGGUUCACCGUUUCAGGCCGCAGGAAGAGGAACGGAGCGAGUCCCGCC

GCGGCGCGAUUCCCUGAGCUGUGGGACGUGCACCCAGGACUCGGCUCACA

CAUGCAGUUCGCUUUCCUGUUGGUGGGGGAACGCCGAUCGUGCGCAUCC

GUCACCCCUCGCCGGCAGUGGGGCUUGUGAACCCCCAAACCUGACUGAC

UGGGCCAGUGUGCU).

In certain embodiments, the oligonucleotide includes a sequence which is complementary or near-complementary to some portion of the 11-nucleotide region having the sequence 5'-CUAACCCUAAC-3' (SEQ ID NO:23) The oligonucleotide having this sequence (TAGGGTTAGACAA; SEQ ID NO:12) and N3'→P5' thiophosphoramidate (NPS) linkages is designated herein as GRN163. See, for example, Asai et al., Cancer Research 63:3931-3939 (2003) and Gryaznov et al., Nucleosides Nucleotides Nucleic Acids 22(5-8):577-81 (2003). Another target region is the region spanning nucleotides 137-179 of hTR (see Pruzan et al., Nucl. Acids Research, 30:559-568, 2002). Within this region, the sequence spanning 141-153 is a preferred target. PCT publication WO 98/28442 describes the use of oligonucleotides of at least 7 nucleotides in length to inhibit telomerase, where the oligonucleotides are designed to be complementary to accessible portions of the hTR sequence outside of the template region, including nucleotides 137-196, 290-319, and 350-380 of hTR. Preferred hTR targeting sequence are given below, and identified by SEQ ID NOS: 2-22. In certain embodiments, the oligonucleotide of the telomerase inhibitor has a sequence targeting human telomerase RNA (hTR), including but not limited to the sequences:

| hTR Targeting Sequence | Region of SEQ ID NO: 1 | SEQ ID NO: |
|---|---|---|
| ACATTTTTGTTTGCTCTAG | 160-179 | 2 |
| GCTCTAGAATGAACGGTGGAAGGCGGCAGG | 137-166 | 3 |
| GTGGAGGCGGCAGG | 137-151 | 4 |
| GGAAGGCGGCAGG | 137-149 | 5 |
| GTGGAAGGCGGCA | 139-151 | 6 |
| GTGGAAGGCGG | 141-151 | 7 |
| CGGTGGAAGGCGG | 141-153 | 8 |
| ACGGTGGAAGGCG | 142-154 | 9 |
| AACGGTGGAAGGCGGC | 143-155 | 10 |
| ATGAACGGTGGAAGGCGG | 144-158 | 11 |
| TAGGGTTAGACAA | 42-54 | 12 |
| CAGTTAGGGTTAG | 46-58 | 13 |
| TAGGGTTAGACA | 42-53 | 14 |
| TAGGGTTAGAC | 42-52 | 15 |
| GTTAGGGTTAG | 46-56 | 16 |
| GTTAGGGTTAGAC | 44-56 | 17 |
| GTTAGGGTTAGACAA | 42-56 | 18 |
| GGGTTAGAC | 44-52 | 19 |
| CAGTTAGGG | 50-58 | 20 |
| CCCTTCTCAGTT | 54-65 | 21 |
| CGCCCTTCTCAG | 56-67 | 22 |

Telomerase inhibitors of the present disclosure include a lipid moiety linked to the 5' and/or 3' end of the oligonucleotide. In some instances, structural group provides for superior cellular uptake properties, such that an equivalent biological effect may be obtained using smaller amounts of the conjugated oligonucleotide compared to the unmodified form. The lipid moiety may be an aliphatic hydrocarbon or fatty acid, such as derivatives of hydrocarbons and fatty acids. For instance, the lipid moiety may be saturated straight chain compounds having 14-20 carbons, such as myristic (tetradecanoic) acid, palmitic (hexadecanoic) acid, and stearic (octadecanoic) acid, and their corresponding aliphatic hydrocarbon forms, tetradecane, hexadecane and octadecane. Examples of other lipid moieties include sterols, such as cholesterol, and substituted fatty acids and hydrocarbons, particularly polyfluorinated forms of these groups. In certain embodiments, the lipid moiety includes one or more derivatives such as amine, amide, ester and carbamate derivative of the lipid moiety. In one example, the lipid moiety is a palmitoyl (C16) moiety, such as palmitoyl amide. The lipid moiety may be conjugated to the oligonucleotide through a linker, such as a glycerol or aminoglycerol linker.

In some embodiments, the telomerase inhibitor is a compound as described in U.S. Pat. No. 9,375,485, the disclosure of which is herein incorporated by reference. In certain embodiments, the telomerase inhibitor is imetelstat (5' palmitoylated 13-mer thiophosphoramidate oligonucleotide composed of the sequence 5'-TAGGGTTAGACAA-3' (SEQ ID NO: 12)) or a pharmaceutically acceptable salt thereof, such as imetelstat sodium (GRN163L):

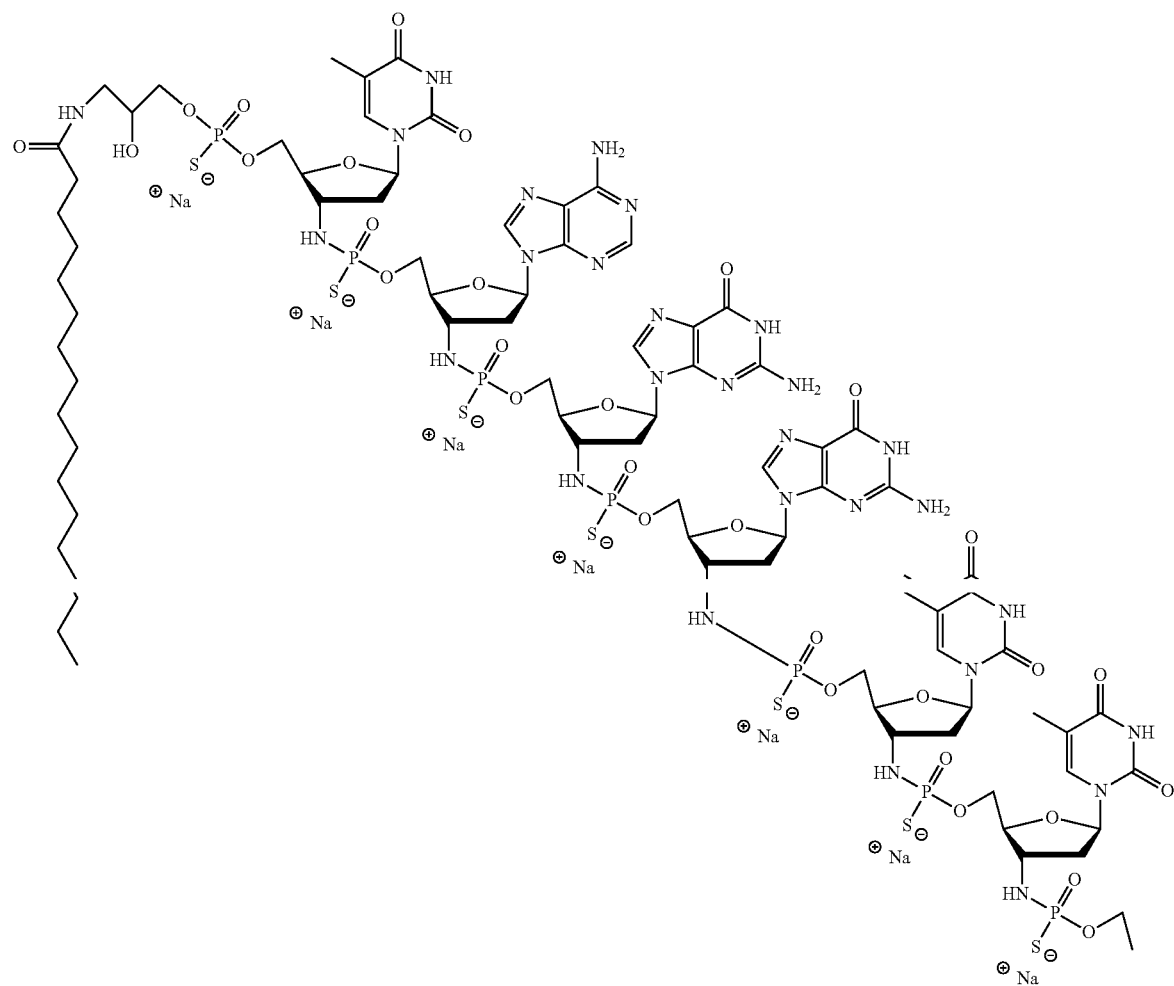

-continued

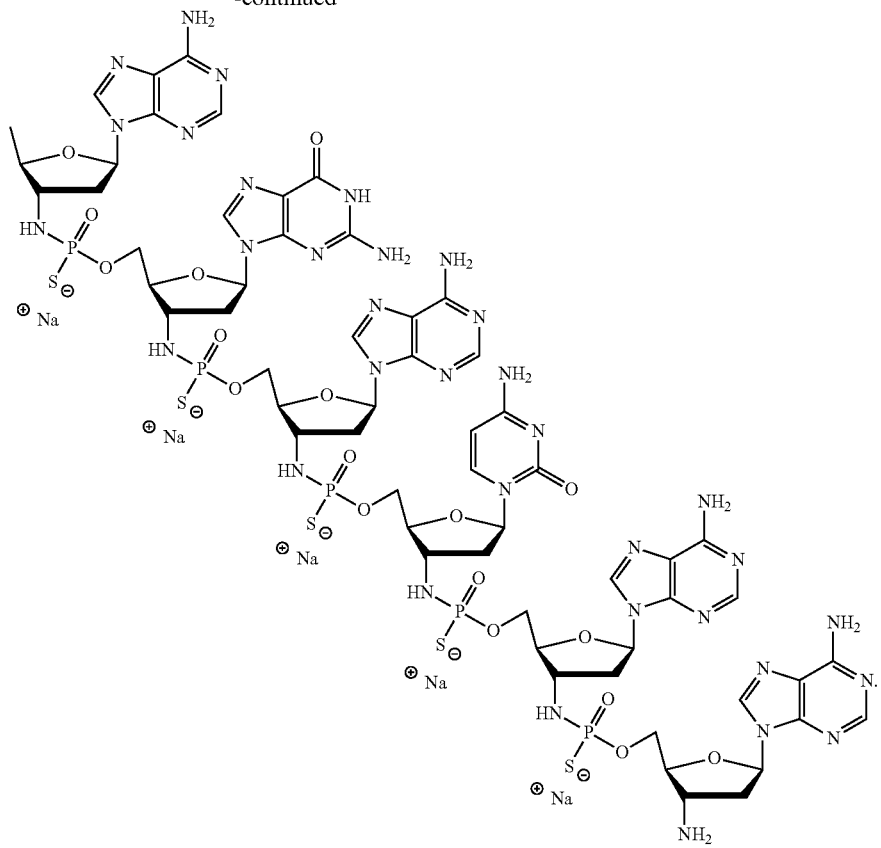

In practicing the subject methods, the amount of JAK inhibitor or pharmaceutically acceptable salt administered to the subject may vary, ranging from about 1 mg/day to about 600 mg/day, such as from about 10 mg/day to about 550 mg/day, such as from 10 mg/day to about 400 mg/day, such as from about 15 mg/day to about 300 mg/day, such as from about 20 mg/day to about 200 mg/day, such as from about 25 mg/day to about 100 mg/day and including from about 30 mg/day to about 35 mg/day. In certain embodiments, the amount of JAK inhibitor administered to the subject is from about 10 mg/day to about 400 mg/day.

Each dosage of ruxolitinib or pharmaceutically acceptable salt administered to the subject may vary ranging from about 5 mg to about 40 mg, such as from about 7.5 mg to about 27.5 mg, such as from about 10 mg to about 25 mg, such as from about 12.5 mg to about 22.5 mg and including from about 15 mg to about 20 mg. In certain embodiments, the dosage of JAK inhibitor administered to the subject is 5.0 mg, 5.1 mg, 5.2 mg, 5.3 mg, 5.4 mg, 5.5 mg, 5.6 mg, 5.7 mg, 5.8 mg, 5.9 mg, 6.0 mg, 6.1 mg, 6.2 mg, 6.3 mg, 6.4 mg, 6.5 mg, 6.6 mg, 6.7 mg, 6.8 mg, 6.9 mg, 7 mg, 7.1 mg, 7.2 mg, 7.3 mg, 7.4 mg, 7.5 mg, 7.6 mg, 7.7 mg, 7.8 mg, 7.9 mg, 8 mg, 8.1 mg, 8.2 mg, 8.3 mg, 8.4 mg, 8.5 mg, 8.6 mg, 8.7 mg, 8.8 mg, 8.9 mg, 9 mg, 9.1 mg, 9.2 mg, 9.3 mg, 9.4 mg, 9.5 mg, 9.6 mg, 9.7 mg, 9.8 mg, 9.9 mg, 10 mg, 10.1 mg, 10.2 mg, 10.3 mg, 10.4 mg, 10.5 mg, 10.6 mg, 10.7 mg, 10.8 mg, 10.9 mg, 11 mg, 11.1 mg, 11.2 mg, 11.3 mg, 11.4 mg, 11.5 mg, 11.6 mg, 11.7 mg, 11.8 mg, 11.9 mg, 12 mg, 12.1 mg, 12.2 mg, 12.3 mg, 12.4 mg, 12.5 mg, 12.6 mg, 12.7 mg, 12.8 mg, 12.9 mg, 13 mg, 13.1 mg, 13.2 mg, 13.3 mg, 13.4 mg, 13.5 mg, 13.6 mg, 13.7 mg, 13.8 mg, 13.9 mg, 14 mg, 14.1 mg, 14.2 mg, 14.3 mg, 14.4 mg, 14.5 mg, 14.6 mg, 14.7 mg, 14.8 mg, 14.9 mg or 15 mg.

In certain embodiments, the JAK inhibitor ruxolitinib is administered to a subject at a dosage of: 5 mg twice per day when the subject has a baseline platelet count of less than about $100 \times 10^9$/L platelets; 15 mg twice per day when the subject has a baseline platelet count of from about $100 \times 10^9$/L platelets to about $200 \times 10^9$/L platelets; and 20 mg twice per day when the subject has a baseline platelet count of greater than about $200 \times 10^9$/L platelets.

In certain embodiments, the JAK inhibitor is fedratinib or a pharmaceutically acceptable salt thereof and is administered to a subject at a dosage of 400 mg once per day when the subject has a baseline platelet count of greater than or equal to about $50 \times 10^9$/L. In certain instances, the fedratinib or pharmaceutically acceptable salt thereof is administered to a subject at a dosage of 300 mg once per day. In other instances, the fedratinib or pharmaceutically acceptable salt thereof is administered to a subject at a dosage of 200 mg once per day. In still other instances, the fedratinib or pharmaceutically acceptable salt thereof is administered to a subject at a dosage of 100 mg once per day. In yet other instances, the fedratinib or pharmaceutically acceptable salt thereof is administered to a subject at a dosage of less than 100 mg once per day.

In other embodiments, the JAK inhibitor is momelotinib or a pharmaceutically acceptable salt thereof and is administered to a subject at a dosage of 400 mg once per day. In certain instances, the momelotinib or pharmaceutically acceptable salt thereof is administered to a subject at a dosage of 300 mg once per day. In other instances, the momelotinib or pharmaceutically acceptable salt thereof is administered to a subject at a dosage of 200 mg once per day. In some instances, the momelotinib or a pharmaceutically acceptable salt thereof is administered at a dosage of 150 mg twice per day. In still other instances, the momelotinib or pharmaceutically acceptable salt thereof is administered to a subject at a dosage of 100 mg once per day.

In other embodiments, the JAK inhibitor is pacritinib or a pharmaceutically acceptable salt thereof and is administered to a subject at a dosage of from about 50 mg to about 600 mg once per day, such as from about 100 mg to about 500 mg once per day, such as from about 150 mg to about 400 mg once per day, and including from about 200 mg to about 350 mg once per day. In certain instances, the pacritinib or pharmaceutically acceptable salt is administered to a subject at a dosage of from about 50 mg to about 600 mg twice per day, such as from about 100 mg to about 500 mg twice per day, such as from about 150 mg to about 400 mg twice per day, and including from about 200 mg to about 350 mg twice per day. In other instances, the pacritinib or pharmaceutically acceptable salt is administered to a subject at a dosage of 100 mg once per day, or from about 100 mg twice per day or from 200 mg twice per day.

Methods according to certain embodiments also include determining the baseline or pretreatment platelet count of the subject before administering the JAK inhibitor to subject. In these embodiments, methods may include determining a baseline or pretreatment platelet count of the subject and determining an amount of the JAK inhibitor for administering to the subject based on the baseline or pretreatment platelet count of the subject. Any convenient hematology protocol can be used to determine the baseline or pretreatment platelet count of the subject such as with a manual or automated hematology analyzer or with a hemocytometer. The baseline or pretreatment platelet count of the subject may be determined (and the amount of JAK inhibitor to be administered) 1 minute or more before administering the JAK inhibitor dosage to the subject according to embodiments of the methods described herein, such as 2 minutes or more, such as 5 minutes or more, such as 10 minutes or more, such as 15 minutes or more, such as 30 minutes or more, such as 60 minutes or more, such as 2 hours or more, such as 3 hours or more, such as 6 hours or more, such as 12 hours or more and including determining the baseline or pretreatment platelet count of the subject 24 hours before administering the JAK inhibitor to the subject.

Each dosage of JAK inhibitor may be administered to the subject once per day or more, such as twice per day, such as three times per day and including four times per day. In certain embodiments, methods include administering JAK inhibitor to the subject once per day. In other embodiments, methods include administering JAK inhibitor to the subject twice per day. In some instances, the JAK inhibitor is administered to the subject once or more per day in a cycle for a duration of 30 days, 29 days, 28 days, 27 days, 26 days, 25 days, 24 days, 23 days, 22 days, 21 days, 20 days, 19 days, 18 days, 17 days, 16 days, 15 days, 14 days, 13 days, 12 days, 11 days, 10 days, 9 days, 8 days, 7 days, 6 days, 5 days, 4 days, 3 days or 2 days or 1 day. In some instances, the JAK inhibitor is administered to the subject once per day for a duration of from about 1 day to about 30 days, such as once per day for a duration of from about 1 day to about 28 days, from 1 day to 21 days, from 7 days to 14 days. In other instances, the JAK inhibitor is administered to the subject twice per day for a duration of from about 1 day to about 30 days, such as once per day for a duration of from about 1 day to about 28 days, from 1 day to 21 days, from 7 days to 14 days.

The JAK inhibitor may be administered to the subject once or more per day for a duration of from about 1 day to about 21 days, such as from 2 days to about 20 days, such as from about 3 days to about 19 days, such as from about 4 days to about 18 days, such as from about 5 days to about 17 days, such as from about 6 days to about 16 days and including from about 7 days to about 14 days. In one example, methods include administering to the subject a JAK inhibitor once per day for a duration of from about 1 day to about 21 days, such as from 2 days to about 20 days, such as from about 3 days to about 19 days, such as from about 4 days to about 18 days, such as from about 5 days to about 17 days, such as from about 6 days to about 16 days and including administering to the subject a JAK inhibitor once per day for a duration of from about 7 days to about 14 days. In another example, methods include administering to the subject a JAK inhibitor twice per day for a duration of from about 1 day to about 21 days, such as from 2 days to about 20 days, such as from about 3 days to about 19 days, such as from about 4 days to about 18 days, such as from about 5 days to about 17 days, such as from about 6 days to about 16 days and including administering to the subject a JAK inhibitor twice per day for a duration of from about 7 days to about 14 days. In certain embodiments, the JAK inhibitor is administered to the subject at a dosage of about 5 mg twice per day when the subject has a baseline platelet count of less than about $100 \times 10^9$/L platelets; about 15 mg twice per day when the subject has a baseline platelet count of from about $100 \times 10^9$/L platelets to about $200 \times 10^9$/L platelets; or about 20 mg twice per day when the subject has a baseline platelet count of greater than about $200 \times 10^9$/L platelets.

The dosage of telomerase inhibitor, such as imetelstat or imetelstat sodium administered to the subject may vary, ranging from about 4 mg/kg to about 15 mg/kg, such as from about 4.0 mg/kg to about 10 mg/kg, such as from about 6 mg/kg to about 14 mg/kg, such as from about 7 mg/kg to about 13 mg/kg, such as from about 8 mg/kg to about 12 mg/kg, such as from about 7.5 mg/kg to 9.4 mg/kg and including from about 9 mg/kg to about 11 mg/kg. In some embodiments, the dosage of telomerase inhibitor administered to the subject is from about 7.5 mg/kg to about 9.4 mg/kg. For example, the dosage of telomerase inhibitor may be 4.0 mg/kg, 4.1 mg/kg, 4.2 mg/kg, 4.3 mg/kg, 4.4 mg/kg, 4.5 mg/kg, 4.6 mg/kg, 4.7 mg/kg, 4.8 mg/kg, 4.9 mg/kg, 5.0 mg/kg, 5.1 mg/kg, 5.2 mg/kg, 5.3 mg/kg, 5.4 mg/kg, 5.5 mg/kg, 5.6 mg/kg, 5.7 mg/kg, 5.8 mg/kg, 5.9 mg/kg, 6.0 mg/kg, 6.1 mg/kg, 6.2 mg/kg, 6.3 mg/kg, 6.4 mg/kg, 6.5 mg/kg, 6.6 mg/kg, 6.7 mg/kg, 6.8 mg/kg, 6.9 mg/kg, 7 mg/kg, 7.1 mg/kg, 7.2 mg/kg, 7.3 mg/kg, 7.4 mg/kg, 7.5 mg/kg, 7.6 mg/kg, 7.7 mg/kg, 7.8 mg/kg, 7.9 mg/kg, 8 mg/kg, 8.1 mg/kg, 8.2 mg/kg, 8.3 mg/kg, 8.4 mg/kg, 8.5 mg/kg, 8.6 mg/kg, 8.7 mg/kg, 8.8 mg/kg, 8.9 mg/kg, 9 mg/kg, 9.1 mg/kg, 9.2 mg/kg, 9.3 mg/kg, 9.4 mg/kg, 9.5 mg/kg, 9.6 mg/kg, 9.7 mg/kg, 9.8 mg/kg, 9.9 mg/kg, 10 mg/kg, 10.1 mg/kg, 10.2 mg/kg, 10.3 mg/kg, 10.4 mg/kg, 10.5 mg/kg, 10.6 mg/kg, 10.7 mg/kg, 10.8 mg/kg, 10.9 mg/kg, 11 mg/kg, 11.1 mg/kg, 11.2 mg/kg, 11.3 mg/kg, 11.4 mg/kg, 11.5 mg/kg, 11.6 mg/kg, 11.7 mg/kg, 11.8 mg/kg, 11.9 mg/kg, 12 mg/kg, 12.1 mg/kg, 12.2 mg/kg, 12.3 mg/kg, 12.4 mg/kg, 12.5 mg/kg, 12.6 mg/kg, 12.7 mg/kg, 12.8 mg/kg, 12.9 mg/kg, 13 mg/kg. In certain embodiments, the dosage of telomerase inhibitor administered to the subject is about 9.4 mg/kg.

The dosage of the telomerase inhibitor, such as imetelstat or imetelstat sodium, may be administered to the subject in a cycle once every week, once every two weeks (14 days), once every three weeks (21 days) or once every four weeks (28 days), once every 6 weeks, once every 8 weeks, once every 10 weeks, once every 12 weeks. In certain embodiments of the method, imetelstat is administered for 1, 2, 3, 4, 5, 6, 7, 8 or more than 8 dosage cycles, each cycle comprising: intravenous administration of about 4-10 mg/kg imetelstat once every three weeks, intravenous administration of about 4-10 mg/kg imetelstat once every four weeks, intravenous administration of about 4-10 mg/kg imetelstat once every two weeks, or intravenous administration of about 7.5-9.4 mg/kg imetelstat once every three weeks. In certain instance, each dosage cycle comprises intravenous administration of about 7.5-9.4 mg/kg imetelstat once every four weeks. In some cases, each dosage cycle comprises intravenous administration of about 9.4 mg/kg imetelstat about once every three weeks.

In some embodiments, the amount of telomerase inhibitor, such as imetelstat or imetelstat sodium, administered to the individual is from about 0.5 to about 5 mg, about 5 to about 10 mg, about 10 to about 15 mg, about 15 to about 20 mg, about 20 to about 25 mg, about 20 to about 50 mg, about 25 to about 50 mg, about 50 to about 75 mg, about 50 to about 100 mg, about 75 to about 100 mg, about 100 to about 125 mg, about 125 to about 150 mg, about 150 to about 175 mg, about 175 to about 200 mg, about 200 to about 225 mg, about 225 to about 250 mg, about 250 to about 300 mg, about 300 to about 350 mg, about 350 to about 400 mg, about 400 to about 450 mg, or about 450 to about 500 mg. In some embodiments, the amount of a telomerase inhibitor in the effective amount administered to the individual (e.g., a unit dosage form) is in the range of from about 5 mg to about 500 mg, such as about 30 mg to about 300 mg or about 50 mg to about 200 mg. In some embodiments, the concentration of the telomerase inhibitor administered to the individual is dilute (about 0.1 mg/ml) or concentrated (about 180 mg/ml), including for example any of about 0.1 to about 200 mg/ml, about 0.1 to about 180 mg/ml, about 0.1 to about 160 mg/ml, about 0.1 to about 140 mg/ml, about 0.1 to about 120 mg/ml, about 0.1 to about 100 mg/ml, about 0.1 to about 80 mg/ml, about 0.1 to about 60 mg/ml, about 0.1 to about 40 mg/ml, about 0.1 to about 20 mg/ml, about 0.1 to about 10 mg/ml about 2 to about 40 mg/ml, about 4 to about 35 mg/ml, about 6 to about 30 mg/ml, about 8 to about 25 mg/ml, about 10 to about 20 mg/ml, about 12 to about 15 mg/ml, or any of about 0.1 mg/ml, 0.2 mg/ml, 0.3 mg/ml, 0.4 mg/ml, 0.5 mg/ml, 0.6 mg/ml, 0.7 mg/ml, 0.8 mg/ml, 0.9 mg/ml, 1 mg/ml, 1.1 mg/ml, 1.2 mg/ml, 1.3 mg/ml, 1.4 mg/ml, 1.5 mg/ml, 1.6 mg/ml, 1.7 mg/ml, 1.8 mg/ml, 1.9 mg/ml, 2 mg/ml, 2.1 mg/ml, 2.2 mg/ml, 2.3 mg/ml, 2.4 mg/ml, or 2.5 mg/ml. In some embodiments, the concentration of the telomerase inhibitor is at least about any of 0.1 mg/ml, 0.2 mg/ml, 0.3 mg/ml, 0.4 mg/ml, 0.5 mg/ml, 1.3 mg/ml, 1.5 mg/ml, 2 mg/ml, 3 mg/ml, 4 mg/ml, 5 mg/ml, 6 mg/ml, 7 mg/ml, 8 mg/ml, 9 mg/ml, 10 mg/ml, 11 mg/ml, 12 mg/ml, 13 mg/ml, 14 mg/ml, 15 mg/ml, 16 mg/ml, 17 mg/ml, 18 mg/ml, 19 mg/ml, 20 mg/ml, 21 mg/ml, 22 mg/ml, 23 mg/ml, 24 mg/ml, 25 mg/ml, 26 mg/ml, 27 mg/ml, 28 mg/ml, 29 mg/ml, 30 mg/ml, 31 mg/ml, 32 mg/ml, 33 mg/ml, 33.3 mg/ml, 34 mg/ml, 35 mg/ml, 36 mg/ml, 37 mg/ml, 38 mg/ml, 39 mg/ml, 40 mg/ml, 50 mg/ml, 60 mg/ml, 70 mg/ml, 80 mg/ml, 90 mg/ml, 100 mg/ml, 110 mg/ml, 120 mg/ml, 130 mg/ml, 140 mg/ml, 150 mg/ml, 160 mg/ml, 170 mg/ml, 180 mg/ml, 190 mg/ml, 200 mg/ml, 210 mg/ml, 220 mg/ml, 230 mg/ml, 240 mg/ml, or 250 mg/ml.

In embodiments, each dosage of telomerase inhibitor is administered to the subject once every 7 days or more, such as once every 10 days or more, such as once every 14 days or more, such as once every 21 days or more, such as once every 28 days or more and including once every 35 days or more. In some embodiments, the telomerase inhibitor is administered to the subject once every two weeks. In other embodiments, the telomerase inhibitor is administered to the subject once every three weeks. In yet other embodiments, the telomerase inhibitor is administered once every 4 weeks. In some instances, each dosage of telomerase inhibitor is administered to the subject over duration of from about 0.1 hours to about 6 hours, such as from about 0.5 hours to about 5 hours, such as from about 1 hour to about 4 hours and including over a duration of from about 2 hours to about 3 hours. In certain instances, the telomerase inhibitor is administered to the subject over a duration of about 2 hours.

In some embodiments, methods for treating a myeloproliferative neoplasm include administering a JAK inhibitor to a subject for a predetermined duration; pausing administration of the JAK inhibitor; and administering a telomerase inhibitor to the subject within a predetermined period of time after the last dose of the JAK inhibitor. In these embodiments, the JAK inhibitor may be administered for a duration of about 0 days to about 28 days, such as from about 1 day to about 21 days, such as from about 2 days to about 14 days and including from about 2 days to about 7 days. The JAK inhibitor may be administered once per day, twice per day, three times per day or four times per day. The telomerase inhibitor is administered to the subject within 7 days of the last dose of the JAK inhibitor, such as within 6 days, such as within 5 days, such as within 4 days and including within 3 days after discontinuing administration of the JAK inhibitor.

In some embodiments, methods for treating a myeloproliferative neoplasm include administering a telomerase inhibitor to a subject for a predetermined duration; discontinuing administration of the telomerase inhibitor; and administering a JAK inhibitor to the subject within a predetermined period of time after discontinued administration of the telomerase inhibitor. In these embodiments, the JAK inhibitor may be administered for a duration of about 0 days to about 28 days, such as from about 1 day to about 21 days, such as from about 2 days to about 14 days and including from about 2 days to about 7 days. The JAK inhibitor may be administered once per day, twice per day, three times per day or four times per day. This cycle may be repeated for 2, 3, 4, 5, 6 or more times.

In certain embodiments, methods include administering to the subject ruxolitinib or a pharmaceutically acceptable salt thereof once per day for a duration of 0 days to 14 days; and administering imetelstat or a pharmaceutically acceptable salt thereof to the subject within 3 days (e.g., 2 days, 1 day or on the same day) of the last administered dosage of ruxolitinib or pharmaceutically acceptable salt thereof. The imetelstat or a pharmaceutically acceptable salt thereof may be then administered, in these embodiments, once every two weeks, once every three weeks or once every four weeks.

The administration of each pharmaceutical composition can be extended over an extended period of time (such as during maintenance therapy), such as from about a month up to about seven years. In some embodiments, one or more of the JAK inhibitor composition and the telomerase inhibitor composition may be administered over a period of about any of 2, 3, 4, 5, 6, 7, 8, 9, 10, 11, 12, 18, 24, 30, 36, 48, 60, 72, or 84 months. In other embodiments, or more of the JAK inhibitor composition and the telomerase inhibitor composition are administered for the rest of the subject's lifetime.

In embodiments, JAK inhibitor compositions and telomerase inhibitor compositions suitable for practicing the subject methods may be formulated one or more of oral, intravenous, subcutaneous, intramuscular, topical, intraperitoneal, intranasal, inhalation, or intraocular administration. The desired protocol used to administer the JAK inhibitor compositions and the telomerase inhibitor compositions and the appropriate dosage as described herein may, in certain embodiments, be determined by a qualified healthcare professional (e.g., a physician).

Pharmaceutical compositions may include one or more pharmaceutically acceptable carriers. Pharmaceutically acceptable excipients have been amply described in a variety of publications, including, for example, A. Gennaro (2000) "Remington: The Science and Practice of Pharmacy", 20th edition, Lippincott, Williams, & Wilkins; Pharmaceutical Dosage Forms and Drug Delivery Systems (1999) H. C. Ansel et al., eds 7th ed., Lippincott, Williams, & Wilkins; and Handbook of Pharmaceutical Excipients (2000) A. H. Kibbe et al., eds., 3rd ed. Amer. Pharmaceutical Assoc. For example, the one or more excipients may include sucrose, starch, mannitol, sorbitol, lactose, glucose, cellulose, talc, calcium phosphate or calcium carbonate, a binder (e.g., cellulose, methylcellulose, hydroxymethylcellulose, polypropylpyrrolidone, polyvinylpyrrolidone, gelatin, gum arabic, poly(ethylene glycol), sucrose or starch), a disintegrator (e.g., starch, carboxymethylcellulose, hydroxypropyl starch, low substituted hydroxypropylcellulose, sodium bicarbonate, calcium phosphate or calcium citrate), a lubricant (e.g., magnesium stearate, light anhydrous silicic acid, talc or sodium lauryl sulfate), a flavoring agent (e.g., citric acid, menthol, glycine or orange powder), a preservative (e.g., sodium benzoate, sodium bisulfite, methylparaben or propylparaben), a stabilizer (e.g., citric acid, sodium citrate or acetic acid), a suspending agent (e.g., methylcellulose, polyvinylpyrrolidone or aluminum stearate), a dispersing agent (e.g., hydroxypropylmethylcellulose), a diluent (e.g., water), and base wax (e.g., cocoa butter, white petrolatum or polyethylene glycol).

In some embodiments, compositions of interest include an aqueous buffer. Suitable aqueous buffers include, but are not limited to, acetate, succinate, citrate, and phosphate buffers varying in strengths from about 5 mM to about 100 mM. In some embodiments, the aqueous buffer includes reagents that provide for an isotonic solution. Such reagents include, but are not limited to, sodium chloride; and sugars e.g., mannitol, dextrose, sucrose, and the like. In some embodiments, the aqueous buffer further includes a non-ionic surfactant such as polysorbate 20 or 80. In some instances, compositions of interest further include a preservative. Suitable preservatives include, but are not limited to, a benzyl alcohol, phenol, chlorobutanol, benzalkonium chloride, and the like. In many cases, the composition is stored at about 4° C. Formulations may also be lyophilized, in which case they generally include cryoprotectants such as sucrose, trehalose, lactose, maltose, mannitol, and the like. Lyophilized formulations can be stored over extended periods of time, even at ambient temperatures.

In some embodiments, compositions include other additives, such as lactose, mannitol, corn starch or potato starch; with binders, such as crystalline cellulose, cellulose derivatives, acacia, corn starch or gelatins; with disintegrators, such as corn starch, potato starch or sodium carboxymethylcellulose; with lubricants, such as talc or magnesium stearate; and if desired, with diluents, buffering agents, moistening agents, preservatives and flavoring agents.

Where the composition is formulated for injection, the compositions may be formulated by dissolving, suspending or emulsifying the JAK inhibitor or the telomerase inhibitor in an aqueous or nonaqueous solvent, such as vegetable or other similar oils, synthetic aliphatic acid glycerides, esters of higher aliphatic acids or propylene glycol; and if desired, with conventional additives such as solubilizers, isotonic agents, suspending agents, emulsifying agents, stabilizers and preservatives.

Examples

The following examples are put forth so as to provide those of ordinary skill in the art with a complete disclosure and description of how to make and use the present invention, and are not intended to limit the scope of what the inventors regard as their invention nor are they intended to represent that the experiments below are all or the only experiments performed. Efforts have been made to ensure accuracy with respect to numbers used (e.g. amounts, temperature, etc.) but some experimental errors and deviations should be accounted for. Unless indicated otherwise, parts are parts by weight, molecular weight is weight average molecular weight, temperature is in degrees Celsius, and pressure is at or near atmospheric. By "average" is meant the arithmetic mean. Standard abbreviations may be used, e.g., bp, base pair(s); kb, kilobase(s); pl, picoliter(s); s or sec, second(s); min, minute(s); h or hr, hour(s); aa, amino acid(s); kb, kilobase(s); bp, base pair(s); nt, nucleotide(s); i.m., intramuscular(ly); i.p., intraperitoneal(ly); s.c., subcutaneous(ly); and the like.

Materials and Methods

Compounds. Imetelstat sodium (GRN163L) is a 5' palmitoylated 13-mer thiophosphoramidate oligonucleotide composed of the sequence 5'-TAGGGTTAGACAA-3' (SEQ ID NO: 12). Mismatched oligonucleotide (MM) is a 5' palmitoylated 13-mer thiophosphoramidate oligonucleotide composed of the sequence 5'-TAGGTGTAAGCAA-3' (SEQ ID NO: 24). Both compounds were provided by Janssen Research & Development, LLC (Raritan, NJ, USA). ruxolitinib ((3R)-3-Cyclopentyl-3-[4-(7H-pyrrolo[2,3-d]pyrimidin-4-yl)pyrazol-1-yl]propanenitrile) was purchased from Selleck Chemicals LLC (Houston, TX, USA).

Patient Specimens and Cell Preparation. Single-cell suspensions were prepared from the surgically removed spleens of 13 patients (Table 1) with advanced forms of MF requiring therapeutic splenectomy. The JAK2, CALR and MPL mutational of each of these patients is shown in Table 1. Cord blood (CB) collections were provided by the New York Blood Center. CD34$^+$ cells were selected from mononuclear cells using a CD34$^+$ cell selection kit (StemCell Technologies, Vancouver, BC, Canada). CD34$^+$ cells with a purity of ≥90% as analyzed using a FACSCanto Flow Cytometer were used in each experiment.

TABLE 1

| Patient | Gender | Age | Diagnosis | JAK2V617F Allele Burden (%)* | CALR Status* | MPL mutation* |
|---|---|---|---|---|---|---|
| 1 | F | 70 | PV-MF | 85.0 | N/A | WT |
| 2 | M | 64 | PMF | 0 | WT | WT |
| 3 | M | 79 | PMF | 2.4 | WT | WT |
| 4 | M | 67 | PMF | 0 | 46-bp Deletion | WT |
| 5 | F | 45 | PV-MF | 90.0 | WT | WT |
| 6 | F | 64 | PV-MF | 78.0 | WT | WT |
| 7 | M | 76 | PMF | 24.9 | WT | WT |
| 8 | M | 73 | PMF | 85.1 | WT | WT |
| 9 | F | 52 | ET-MF | 0 | Deletion | WT |

TABLE 1-continued

| Patient | Gender | Age | Diagnosis | JAK2V617F Allele Burden (%)* | CALR Status* | MPL mutation* |
|---|---|---|---|---|---|---|
| 10 | M | 58 | PV-MF | 0 | WT | N/A |
| 11 | M | 66 | PMF | 0 | WT | WT |
| 12 | F | 73 | ET-MF | 0.3 | WT | WT |
| 13 | M | 51 | PMF | 28.0 | N/A | WT |

*The JAK2V617F status of each MF patient was determined by analyzing PB granulocytes utilizing real-time allele-specific polymerase chain reaction (AS-PCR) assay. Mutational analysis of CALR was performed by sequencing regions of DNA where known mutations in CALR have been previously described. MPLW515L/K mutations were detected by AS-PCR.
WT: Wild type. N/A: Not Available.

Treating NOD/SCID/IL2R null (NSG) mice transplanted with normal or MF splenic CD34+ cells directly with various drugs alone and in combination. To identify the dose of imetelstat alone which was tolerated by NSG mice and which minimally affected the behavior of normal CD34$^+$ cells, CB CD34$^+$ cells from 8-10 donors were pooled (n=3) and were transplanted (5×10$^5$/mouse) via the tail vein into eight- to nine-week-old sub-lethally irradiated (240 cGy) NSG mice. These mice were then injected a week after transplantation intraperitoneal (IP) with 5, 15, 30 mg/kg of imetelstat or MM/thrice weekly for 4-8 weeks. Two to three months after the discontinuation of imetelstat or MM administration, the mice were sacrificed and the cells were recovered from the bone marrow (BM) of the femurs, tibias, humeri. The presence of human (h) CD45$^+$, CD41a$^+$ and CD34$^+$ cells was determined by mAb staining and flow cytometric analysis.

To examine the effects of imetelstat on MF HSCs, MF splenic CD34$^+$ cells (3-5×10$^5$/mouse, n=3) were shown to achieve significant degrees of human cell chimerism 4 months after their transplantation into NSG mice were utilized. CD34$^+$ cells from these spleens were transplanted into NSG mice and after a week were treated with imetelstat or MM at the dose of 15 mg/kg for 4 weeks. Three months after discontinuation of drug treatment, the presence of cells belonging to various human hematopoietic cell lineages in the BMs of recipient mice was quantitated. In addition, the hCD45$^+$ cells in the BM of the recipient mice were selected using a FACSAria cell sorter. The percentage of JAK2V617F/JAK2$_{total}$ present in the genomic DNA of selected hCD45$^+$ cells from the mice receiving splenic CD34$^+$ cells from a patient with a granulocyte JAK2V617F allele burden of 85.1% was determined using a quantitative real-time (RT)-polymerase chain reaction (PCR) with an allelic discrimination method. If hCD45$^+$ cells were present at ≥0.1% of the nucleated cells in murine BM, human engraftment was noted as having occurred in NSG mice.

Figure 1:
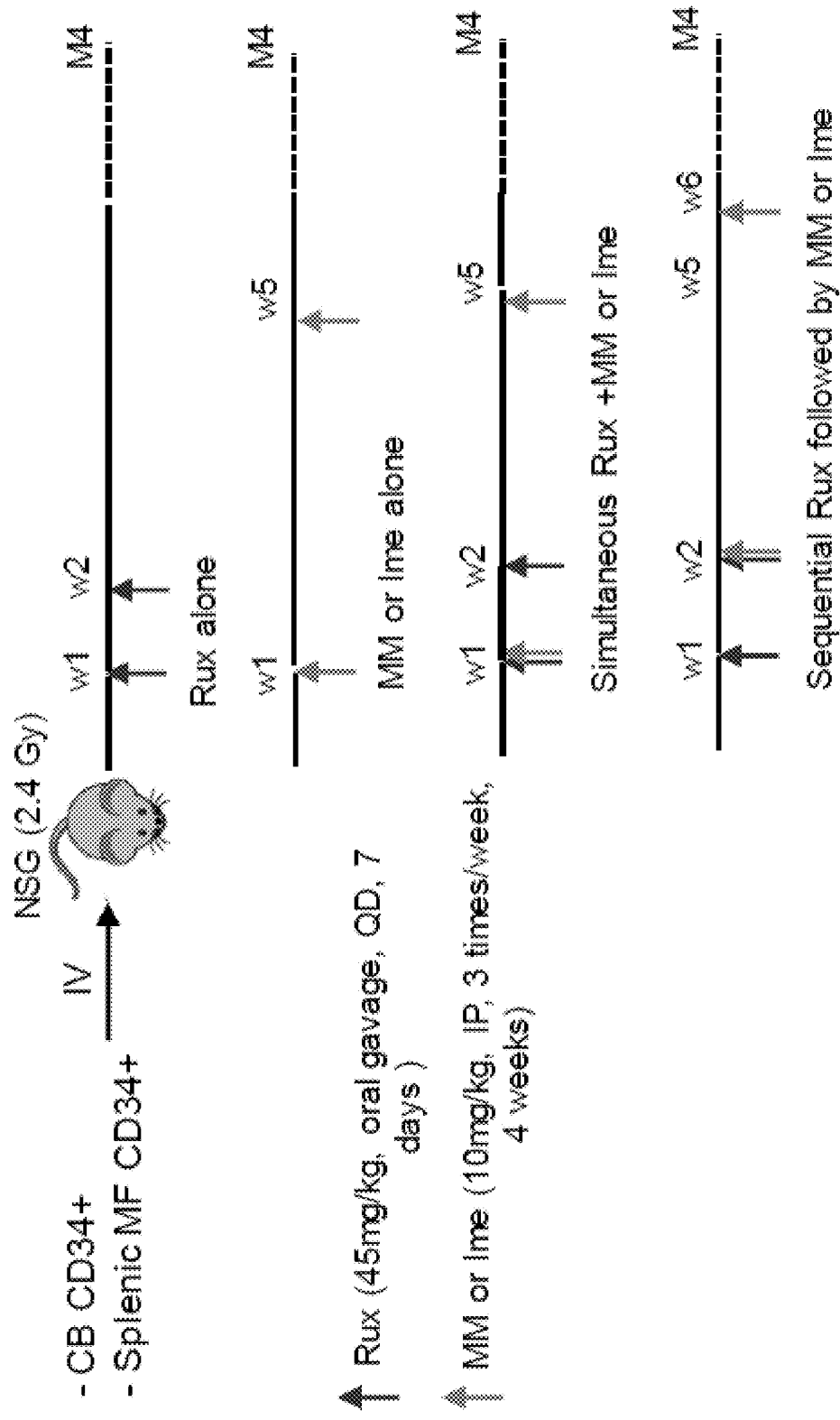
FIG. 1 depicts in vivo treatment design with imetelstat treatment in combination with ruxolitinib according to certain embodiments.

In vivo studies with Rux and imetelstat alone and in combination were performed as depicted in FIG. 1. CB CD34$^+$ cells (n=1) from 12 donors (2.5×10$^5$/mouse) or MF splenic CD34$^+$ cells (3-5×10$^5$/mouse) from 2 patients that have been assessed for the effect of imetelstat alone treatment on MF HSCs were transplanted via the tail vein into eight- to nine-week-old sub-lethally irradiated (240 cGy) NSG mice. One week following the transplantation, transplanted mice were randomly divided into 8 treatment cohorts of 2-3 mice and were treated as follows: Group 1: Rux alone; Group 2: imetelstat or MM alone; Group 3: simultaneous Rux and imetelstat or MM (Rux+Ime); Group 4: Rux followed by imetelstat or MM (Rux→Ime or MM); Group 5: vehicle alone. Rux was given once daily by oral gavage for 1 week at a dose of 45 mg/kg and imetelstat or MM was given three times a week by I.P. injection at 10 mg/kg for 4 weeks. Four months after the transplantation, the mice were sacrificed and analyzed as described above.

Western Blotting. Primary CB and splenic MF CD34$^+$ cells were lysed. Protein lysates were then analyzed by 4-20% SDS-PAGE as previously described. Rabbit anti-hTERT, and corresponding HRP-conjugated secondary antibodies were procured from Cell Signaling Technology, Inc., (Danvers, MA). The proteins were visualized by enhanced chemiluminescence detection (ECL, Amersham Pharmacia Biotech, Piscataway, NJ).

Telomerase activity (TA) assays. A quantitative telomerase detection kit was utilized to measure TA. The TA was measured in 0.01-0.1 g cell lysates by monitoring telomeric repeat synthesis in the presence of a telomere-specific sequence oligonucleotide substrate. The newly synthesized DNA was then detected by PCR. The results were plotted as the number of real-time PCR threshold cycles ($C_T$) required for detection of SYBR green fluorescence resulting from binding to the resultant PCR product. Heat-inactivated telomerase was used as a negative control for cell extracts with each experimental condition. Increased TA was associated with increased double stranded DNA synthesis which required fewer PCR cycles ($C_T$) (e.g. the lower the $C_T$ number, the higher the TA).

Telomerase length analysis. For analysis of telomere length, a flow-fluorescence in situ hybridization (Flow-FISH) was performed with a Telomere PNA Kit/FITC for Flow Cytometry. An equal number of primary MF or normal CB CD34$^+$ cells were re-suspended in micro-centrifuge tubes either in the presence of hybridization solution without FITC-conjugated peptide nucleic acid (PNA) telomere probe or in hybridization solution containing the probe. The tubes were placed in a pre-warmed heating block adjusted to 82° C. for 10 mins allowing for the sample DNA to be denatured. The tubes were then placed in the dark at room temperature (RT) overnight for the probe to hybridize with TTAGGG telomere repeats. The hybridization was followed by two 10-minute post-hybridization washes with a wash solution at 40° C. After the last wash step, cells were stained with CD34 and CD38 mAb and incubated with the DNA solution for 2-3 hours prior to flow cytometric analysis. Telomere fluorescence intensity (TFI) of CD34$^+$, CD34$^+$CD38$^-$ and CD34$^+$CD38$^+$ cells from each sample were calculated as following: TFI=Mean fluorescence intensity (MFI) of FITC-PNA with probe-MFI of FITC-PNA without probe. The higher TFI, the longer telomere.

Figure 2:
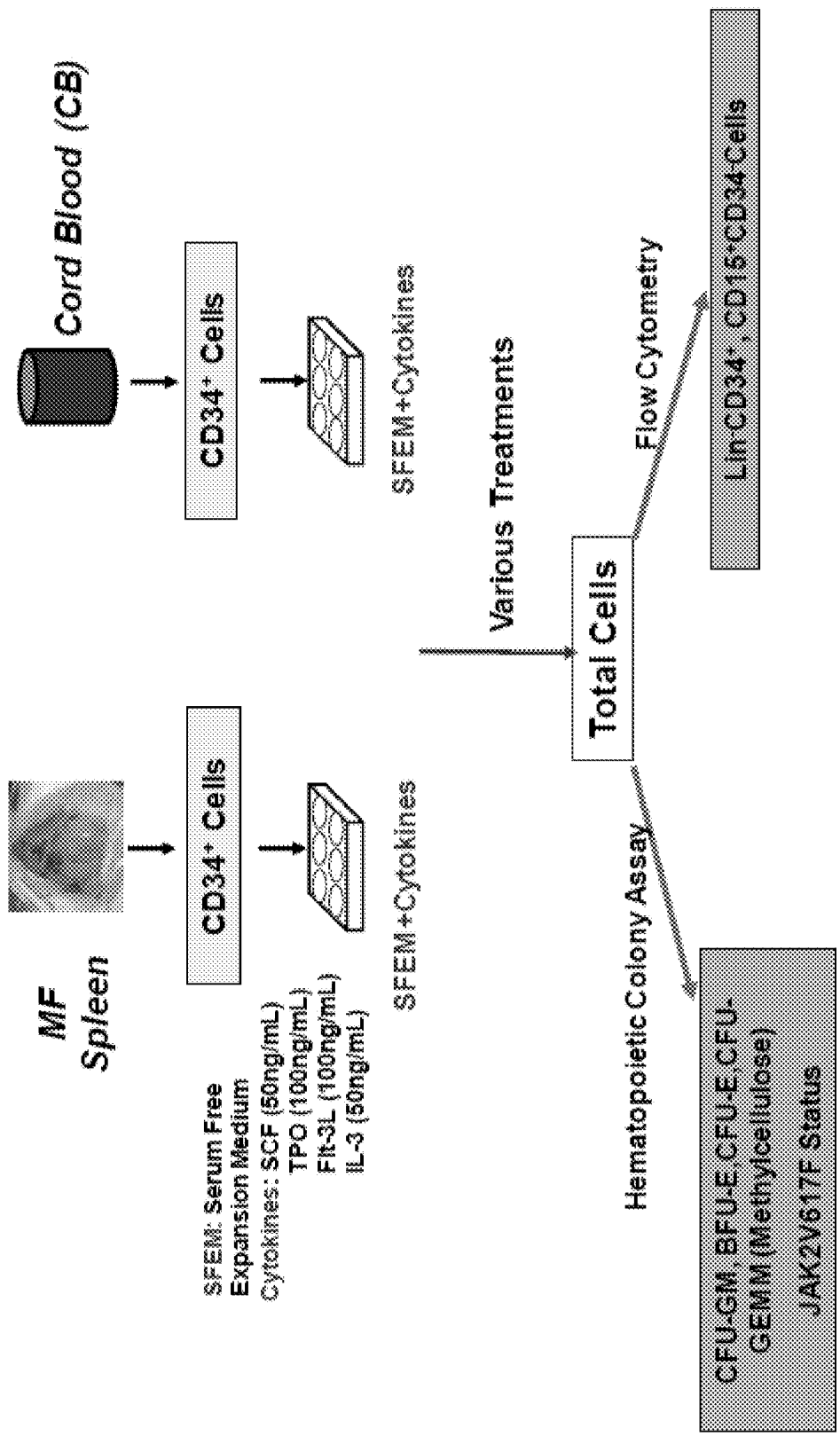
FIG. 2 depicts hematopoietic progenitor cell (HPC) assay, with imetelstat treatment in combination with ruxolitinib in vitro according to certain embodiments.
Figure 3:
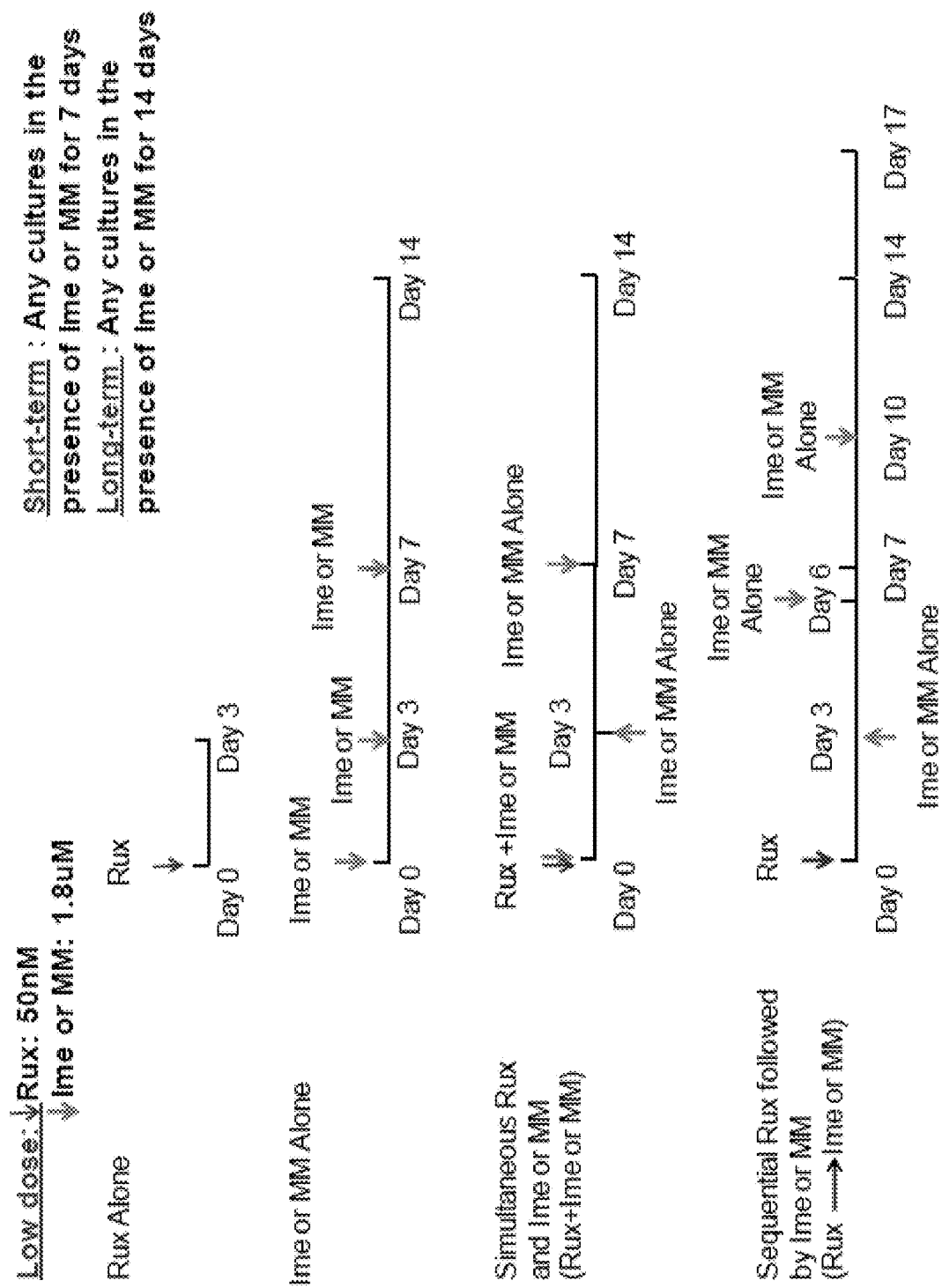
FIG. 3 depicts in vitro treatment design with imetelstat treatment in combination with ruxolitinib according to certain embodiments.

Treatment of MF and normal CD34$^+$ cells with doses of Rux and Imetelstat alone and in combination. In vitro studies indicate that while the number of CB CD34$^+$ cells were decreased only to a limited degree following the treatment with various doses of Rux (50-500 nM), the absolute number of MF splenic CD34$^+$ cells decreased in a dose dependent fashion. A 50% inhibition of MF CD34$^+$ cell proliferation and CFU-GM formation was achieved by using 150 nM Rux. Based on these observations and the results from in vitro studies of imetelstat, 50 nM of Rux and 1.8 M imetelstat were chosen to determine if a sequential or a simultaneous combination of these two drugs had an additive or synergistic effect on MF HSCs/HPCs. FIG. 2 depicts a schematic diagram of the in vitro combination study design and FIG. 3 shows the drug treatment strategy. Briefly, CB (n=3) or MF (JAK2V617F+, n=3; JAK2V617F, n=4) (2.5×10$^4$/mL) CD34$^+$ cells were incubated in serum free expansion medium (SFEM, StemCell Technologies) supplemented with 50 ng/ml SCF, 100 ng/ml FLT-3 ligand (FLT-3L), 100 ng/ml TPO, and 50 ng/ml IL-3 (Gemini Bio-Products) in the presence of Rux (50 nM) alone for 3 days or imetelstat (1.8 uM) alone for 7 days (short-term treatment) or 14 days (long-term treatment). For simultaneous combination treatment, CD34$^+$ cells were exposed to Rux and imetelstat for 3 days and were washed. Cells were then exposed to imetelstat again for additional 4 days or 11 days. For sequential combination treatment, CD34$^+$ cells were incubated in the presence of Rux alone for 3 days, followed by imetelstat alone for 7 or 14 days. For the three treatment strategies containing imetelstat, cells were dosed in total three times with imetelstat. Three days after Rux alone treatment and 7 or 14 days after each treatment with imetelstat, cells were enumerated and stained with CD34, a lineage cocktail, and CD15 mAbs and analyzed flow cytometrically. The absolute numbers of Lin$^-$ CD34$^+$ (phenotypically defined HSC/HPC) and CD15$^+$CD34$^-$ (myeloid) cells generated in the cultures were calculated by multiplying the total viable cell numbers by the percentage of CD34$^+$Lin$^-$ and CD15$^+$CD34$^-$ cells. In addition, parallel cultures to which MM or vehicle alone was added were performed.

HPC assays. A fraction of cells harvested from the above cultures were also analyzed in methylcellulose to which a cytokine cocktail was added according to the manufacturer's instructions (StemCell Technologies). The numbers of colonies were enumerated after 12 to 14 days of incubation. Individual CFU-GM colonies (20-38 colonies/treatment group/patient) were plucked and analyzed for the presence of JAK2V617F using a nested allele-specific PCR. The percentage of JAK2V617F$^+$ CFU-GM was then determined.

Statistical analysis. Results are reported as the mean±SD. Statistical significance was determined using a two tailed Student's t test. All P values were two sided, and P values less than 0.05 were considered significant.

Results and Discussion

Figure 4:
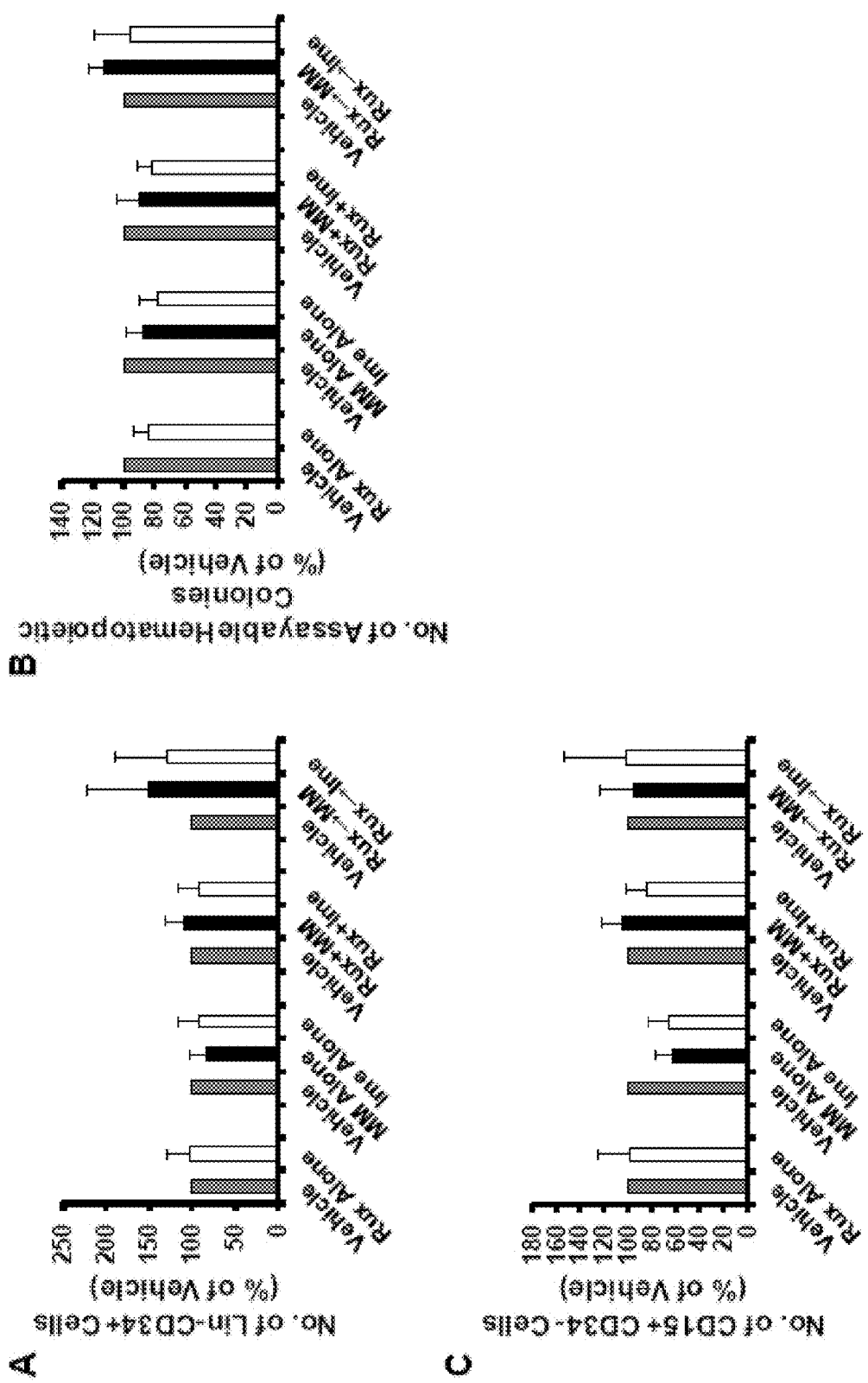
FIG. 4 depicts short-term in vitro combination treatment of normal $CD34^+$ cells with of imetelstat and ruxolitinib according to certain embodiments. Normal CB $CD34^+$ cells were treated with vehicle alone, ruxolitinib (Rux, 50 nM)

Sequential treatment with imetelstat in combination with Rux has additive inhibitory activity against MF HSCs and HPCs. As shown in FIGS. 4-5, neither dose of Rux alone (50 nM), imetelstat alone (1.8µM), simultaneous or sequential short-term (FIG. 4) or long-term (FIG. 5) of combinations of these drugs affected the numbers of normal phenotypically defined CB HSC and functionally defined HPC production and normal myeloid cell generation. The effects of these two drugs alone and in combination were assessed on MF HSCs/HPCs. As shown in FIGS. 6-7, Rux alone reduced the numbers of assayable HPCs (CFU-GM+BFU-E+CFU-GEMM, P=9.69E-06, FIG. 6-7, panel B) and the number of mature myeloid cells (FIGS. 6-7, panel C, P=0.001) generated in cultures of splenic MF CD34$^+$ cells. However, neither short-term imetelstat alone nor short-term simultaneous or sequential drug combination treatment affected the numbers of phenotypically defined MF HSCs, functionally defined HPCs produced and myeloid cell generation. Sequential long-term treatment of splenic MF CD34$^+$ cells with 50 nM doses of Rux followed by 1.8 M doses of imetelstat, by contrast, resulted in significant reductions in the numbers of Lin$^-$CD34$^+$ cells, assayable HPCs and mature myeloid cells (FIG. 7). Such sequential combination treatment suppressed the production of MF Lin$^-$CD34$^+$ cells (P=0.001 versus Rux alone; P=0.059 versus Imetelstat alone, FIG. 7, panel A) and assayable HPCs (P=0.02 versus Rux alone; P=0.05 versus imetelstat alone, FIG. 7, panel B) to an even greater degree than either drug alone treatment. The number of CD15$^+$CD34$^-$ cells generated in cultures exposed to sequential long-term treatment with the same drug combination was reduced to a similar degree as that generated in cultures in the presence of Rux alone or imetelstat alone (FIG. 6, panel C, FIG. 7, panel C). However, such inhibitory effects on Lin$^-$CD34$^+$ cells and assayable HPCs were not observed in cultures receiving long-term simultaneous treatment with the same drug combination (FIG. 7). These findings indicate that sequential treatment with Rux followed by imetelstat results in an additive inhibitory effect against phenotypically defined MF HSCs and functionally defined MF HPCs but does not affect their normal counterpart. In order to determine whether such combination treatments selectively affected mutant MF HPCs, individual CFU-GM colonies generated were chosen and genotyped them for the presence of JAK2V617F. As shown in FIG. 8, sequential long-term combination treatment of SP7 CD34$^+$ cells with Rux and imetelstat resulted in a reduction in both the percentage (Vehicle alone: 94.2%; Rux→MM:88.9%; Rux→imetelstat: 75%, FIG. 8, panel A) and absolute numbers of JAK2V617F$^+$ myeloid progenitors (Relative to vehicle alone: Rux→MM: 50.3%; Rux→imetelstat: 22.7%, FIG. 8, panel B), which was even lower than imetelstat alone treatment (Relative to vehicle alone: 72.4%, FIG. 8, panel B) or simultaneous combination treatment (Relative to vehicle alone: 60.3%, FIG. 8, panel B). The reduction in the absolute number of JAK2V617F$^+$ myeloid progenitors was also seen with another patient cells (Pt13, Absolute numbers relative to vehicle alone: Rux→MM: 97.5%; Rux→imetelstat: 44.1%, FIG. 8, panel C). These findings suggest an additive inhibitory activity against malignant MF HPCs can be achieved by sequential treatment with Rux followed by imetelstat.

Sequential combination treatment with imetelstat and Rux has additive inhibitory activity against MF SRCs. An assessment was conducted of whether combination treatment with imetelstat (10 mg/kg) and Rux (45 mg/kg) had additive effect on normal or MF HSCs by directly treating NSG mice transplanted with CB or MF CD34$^+$ cells with these two drugs. FIG. 9, panels A and D show the FACS plots of hCD45$^+$ (FIG. 9, panel A) and hCD34$^+$ cells (FIG. 9, panel D) present in the marrow of mice transplanted with CB CD34$^+$ cells post-treatment with these drugs alone or in combination. These treatments did not or only resulted in a mild reduction in the degree of hCD45$^+$ cell chimerism and hCD34$^+$ cell generation in the marrows (FIG. 9, panels B, E) and spleens (FIG. 9, panels C, F) of the recipient mice receiving normal CB grafts. By contrast, both simultaneous and sequential combination treatment of mice transplanted with splenic CD34$^+$ cells from Pt5 with an equal dose of Rux and imetelstat resulted in greater reductions in the absolute number of hCD45$^+$ cells in the marrow (FIG. 10, panel B) and spleen (FIG. 10, panel C) as compared with either drug alone treatment. Moreover, sequential combination treatment resulted in an even greater reduction in the number of hCD45$^+$ cells than simultaneous combination treatment (FIG. 10, panels B-C). Furthermore, a greater reduction in the absolute number of hCD34$^+$ cells was observed with sequential but not simultaneous combination treatment as compared with either drug alone treatment in the marrow of mice transplanted with Pt 5 CD34$^+$ cells (FIG. 10, panel E). Since no hCD34$^+$ cells were detected in the spleen of mice transplanted with graft from Pt 5, the effects of these treatments on hCD34$^+$ cells in the spleen of transplanted mice could not be evaluated. The depletion of MF SRC by sequential combination treatment was also achieved in mice receiving splenic CD34$^+$ cells from another patient, Pt10 (FIG. 11), while treatment with either drug alone had limited inhibitory effects on MF SRCs from this patient. These findings suggest that sequential treatment with doses of Rux followed by imetelstat has at least an additive activity in depleting MF long-term HSCs. This same sequential drug schema did not affect normal HSC function. In addition, as shown in FIGS. 12A-12B, sequential combination treatment with doses of each drug resulted in a similar reduction of body weight in mice receiving either normal (FIG. 12A) or MF splenic CD34+ cells (FIG. 12B) as compared to mice receiving the same dose (10 mg/kg) of imetelstat alone. Collectively, these observations suggest that sequential treatment with Rux followed by imetelstat represents an effective therapeutic strategy that is capable of eliminating MF stem cells with an acceptable toxicity profile.

Although the foregoing invention has been described in some detail by way of illustration and example for purposes of clarity of understanding, it is readily apparent to those of ordinary skill in the art in light of the teachings of this invention that certain changes and modifications may be made thereto without departing from the spirit or scope of the appended claims.

Accordingly, the preceding merely illustrates the principles of the invention. It will be appreciated that those skilled in the art will be able to devise various arrangements which, although not explicitly described or shown herein, embody the principles of the invention and are included within its spirit and scope. Furthermore, all examples and conditional language recited herein are principally intended to aid the reader in understanding the principles of the invention and the concepts contributed by the inventors to furthering the art, and are to be construed as being without limitation to such specifically recited examples and conditions. Moreover, all statements herein reciting principles, aspects, and embodiments of the invention as well as specific examples thereof, are intended to encompass both structural and functional equivalents thereof. Additionally, it is intended that such equivalents include both currently known equivalents and equivalents developed in the future, i.e., any elements developed that perform the same function, regardless of structure. Moreover, nothing disclosed herein is intended to be dedicated to the public regardless of whether such disclosure is explicitly recited in the claims.

The scope of the present invention, therefore, is not intended to be limited to the exemplary embodiments shown and described herein. Rather, the scope and spirit of present invention is embodied by the appended claims. In the claims, 35 U.S.C. § 112(f) or 35 U.S.C. § 112(6) is expressly defined as being invoked for a feature in the claim only when the exact phrase "means for" or the exact phrase "step for" is recited at the beginning of such feature in the claim; if such exact phrase is not used in a feature in the claim, then 35 U.S.C. § 112(f) or 35 U.S.C. § 112(6) is not invoked.

What is claimed is:

1. A method of treating a subject having a myeloproliferative neoplasm, the method comprising sequentially administering to the subject ruxolitinib or a pharmaceutically acceptable salt thereof, followed by imetelstat or a pharmaceutically acceptable salt thereof.

2. The method according to claim 1, wherein the method comprises:
    administering on a first day a dosage of ruxolitinib or pharmaceutically acceptable salt thereof and a dosage of imetelstat or pharmaceutically acceptable salt thereof; and
    administering a dosage of ruxolitinib or pharmaceutically acceptable salt thereof once or twice per day for a duration of from about 20 days to about 27 days after the first day.

3. The method according to claim 2, wherein the dosage of ruxolitinib or pharmaceutically acceptable salt thereof is administered twice on the first day.

4. The method according to claim 1, wherein the method comprises:
    administering to the subject ruxolitinib or a pharmaceutically acceptable salt thereof once or twice per day for a duration of from about 14 days to 21 days; and
    administering to the subject one or more doses of imetelstat or pharmaceutically acceptable salt thereof during the period from about 1 day to about 7 days after the last administered dosage of the ruxolitinib or pharmaceutically acceptable salt thereof.

5. The method according to claim 1, wherein ruxolitinib or a pharmaceutically acceptable salt thereof is administered to the subject at a dosage of about 10 mg/day to about 400 mg/day.

6. The method according to claim 1, wherein imetelstat or a pharmaceutically acceptable salt thereof is administered to the subject at a dosage of from about 7.5 mg/kg to about 9.4 mg/kg.

7. The method according to claim 1, wherein imetelstat or a pharmaceutically acceptable salt thereof is administered to the subject by intravenous infusion over a duration of from about 1 hour to about 3 hours.

8. The method according to claim 1, wherein ruxolitinib or a pharmaceutically acceptable salt thereof is administered to the subject once per day.

9. The method according to claim 1, wherein the ruxolitinib or a pharmaceutically acceptable salt thereof is administered to a subject at a dosage of:
    5 mg twice per day when the subject has a baseline platelet count of less than about $100 \times 10^9$/L platelets;
    15 mg twice per day when the subject has a baseline platelet count of from about $100 \times 10^9$/L platelets to about $200 \times 10^9$/L platelets; and
    20 mg twice per day when the subject has a baseline platelet count of greater than about $200 \times 10^9$/L platelets.

10. The method according to claim 1, wherein the telomerase inhibitor is imetelstat sodium.

11. The method according to claim 1, wherein the method comprises:
    administering to the subject ruxolitinib or a pharmaceutically acceptable salt thereof once or twice per day for a duration of 0 days to 21 days; and
    administering to the subject one dose or more of imetelstat or a pharmaceutically acceptable salt thereof within 7 days of the last administered dosage of ruxolitinib or pharmaceutically acceptable salt thereof.

12. The method according to claim 1, wherein the myeloproliferative neoplasm is selected from myelofibrosis (MF), myelodysplastic syndrome (MDS), Essential Thrombocythemia (ET), Polycythemia vera (PV), Chronic Myelogenous Leukemia (CML), chronic neutrophilic leukemia, chronic eosinophilic leukemia and acute myeloid leukemia (AML).

13. A method of inducing apoptosis of a myeloproliferative neoplasm cell, the method comprising sequentially contacting the cell with ruxolitinib or a pharmaceutically acceptable salt thereof, followed by imetelstat or a pharmaceutically acceptable salt thereof sufficient to induce apoptosis.

14. The method according to claim 13, wherein the myeloproliferative neoplasm cell is a myelofibrosis hematopoietic stem cell (HSC) or a malignant hematopoietic progenitor cell (HPC).

15. The method according to claim 13, wherein the ruxolitinib or a pharmaceutically acceptable salt thereof and the imetelstat or a pharmaceutically acceptable salt thereof are contacted with the myeloproliferative neoplasm cell in vitro.

* * * * *

SEQUENCE LISTING

```
<160> NUMBER OF SEQ ID NOS: 24

<210> SEQ ID NO 1
<211> LENGTH: 554
<212> TYPE: RNA
<213> ORGANISM: Artificial sequence
<220> FEATURE:
<223> OTHER INFORMATION: synthetic sequence

<400> SEQUENCE: 1
ggguugcgga gguggggccu gggaggggug guggccauuu uuugucuaac ccuaacugag      60
aagggcguag gcgccgugcu uuugcucccc gcgcgcuguu uuucucgcug acuuucagcg     120
ggcggaaaag ccucggccug ccgccuucca ccguucauuc uagagcaaac aaaaaauguc     180
agcugcuggc ccguucgccu cccggggacc ugcggcgggu cgccugccca gcccccgaac     240
cccgccugga gccgcggucg gcccggggcu ucuccggagg cacccacugc caccgcgaag     300
aguugggcuc ugucagccgc gggucucucg ggggcgaggg cgagguucac cguuucaggc     360
cgcaggaaga ggaacggagc gaguccccgcc gcggcgcgau ucccugagcu gugggacgug     420
cacccaggac ucggcucaca caugcaguuc gcuuuccugu uggugggggg aacgccgauc     480 gucgcaucc gucaccccuc gccggcagug ggggcuugug aaccccaaa ccugacugac     540 ugggccagug ugcu                                                       554

<210> SEQ ID NO 2
<211> LENGTH: 20
<212> TYPE: DNA
<213> ORGANISM: Artificial sequence
<220> FEATURE:
<223> OTHER INFORMATION: synthetic sequence

<400> SEQUENCE: 2
acattttttg tttgctctag                                                  20

<210> SEQ ID NO 3
<211> LENGTH: 30
<212> TYPE: DNA
```

```
<213> ORGANISM: Artificial sequence
<220> FEATURE:
<223> OTHER INFORMATION: synthetic sequence

<400> SEQUENCE: 3
gctctagaat gaacggtgga aggcggcagg                                    30

<210> SEQ ID NO 4
<211> LENGTH: 14
<212> TYPE: DNA
<213> ORGANISM: Artificial sequence
<220> FEATURE:
<223> OTHER INFORMATION: synthetic sequence

<400> SEQUENCE: 4
gtggaggcgg cagg                                                     14

<210> SEQ ID NO 5
<211> LENGTH: 13
<212> TYPE: DNA
<213> ORGANISM: Artificial sequence
<220> FEATURE:
<223> OTHER INFORMATION: synthetic sequence

<400> SEQUENCE: 5
ggaaggcggc agg                                                      13

<210> SEQ ID NO 6
<211> LENGTH: 13
<212> TYPE: DNA
<213> ORGANISM: Artificial sequence
<220> FEATURE:
<223> OTHER INFORMATION: synthetic sequence

<400> SEQUENCE: 6
gtggaaggcg gca                                                      13

<210> SEQ ID NO 7
<211> LENGTH: 11
<212> TYPE: DNA
<213> ORGANISM: Artificial sequence
<220> FEATURE:
<223> OTHER INFORMATION: synthetic sequence

<400> SEQUENCE: 7
gtggaaggcg g                                                        11

<210> SEQ ID NO 8
<211> LENGTH: 13
<212> TYPE: DNA
<213> ORGANISM: Artificial sequence
<220> FEATURE:
<223> OTHER INFORMATION: synthetic sequence

<400> SEQUENCE: 8
cggtggaagg cgg                                                      13

<210> SEQ ID NO 9
<211> LENGTH: 13
<212> TYPE: DNA
<213> ORGANISM: Artificial sequence
<220> FEATURE:
<223> OTHER INFORMATION: synthetic sequence

<400> SEQUENCE: 9
acggtggaag gcg                                                      13
```

```
<210> SEQ ID NO 10
<211> LENGTH: 16
<212> TYPE: DNA
<213> ORGANISM: Artificial sequence
<220> FEATURE:
<223> OTHER INFORMATION: synthetic sequence

<400> SEQUENCE: 10
aacggtggaa ggcggc                                                         16

<210> SEQ ID NO 11
<211> LENGTH: 18
<212> TYPE: DNA
<213> ORGANISM: Artificial sequence
<220> FEATURE:
<223> OTHER INFORMATION: synthetic sequence

<400> SEQUENCE: 11
atgaacggtg gaaggcgg                                                       18

<210> SEQ ID NO 12
<211> LENGTH: 13
<212> TYPE: DNA
<213> ORGANISM: Artificial sequence
<220> FEATURE:
<223> OTHER INFORMATION: synthetic sequence

<400> SEQUENCE: 12
tagggttaga caa                                                            13

<210> SEQ ID NO 13
<211> LENGTH: 13
<212> TYPE: DNA
<213> ORGANISM: Artificial sequence
<220> FEATURE:
<223> OTHER INFORMATION: synthetic sequence

<400> SEQUENCE: 13
cagttagggt tag                                                            13

<210> SEQ ID NO 14
<211> LENGTH: 12
<212> TYPE: DNA
<213> ORGANISM: Artificial sequence
<220> FEATURE:
<223> OTHER INFORMATION: synthetic sequence

<400> SEQUENCE: 14
tagggttaga ca                                                             12

<210> SEQ ID NO 15
<211> LENGTH: 11
<212> TYPE: DNA
<213> ORGANISM: Artificial sequence
<220> FEATURE:
<223> OTHER INFORMATION: synthetic sequence

<400> SEQUENCE: 15
tagggttaga c                                                              11

<210> SEQ ID NO 16
<211> LENGTH: 11
<212> TYPE: DNA
<213> ORGANISM: Artificial sequence
<220> FEATURE:
```

<223> OTHER INFORMATION: synthetic sequence

<400> SEQUENCE: 16
gttagggtta g                                                        11

<210> SEQ ID NO 17
<211> LENGTH: 13
<212> TYPE: DNA
<213> ORGANISM: Artificial sequence
<220> FEATURE:
<223> OTHER INFORMATION: synthetic sequence

<400> SEQUENCE: 17
gttagggtta gac                                                      13

<210> SEQ ID NO 18
<211> LENGTH: 15
<212> TYPE: DNA
<213> ORGANISM: Artificial sequence
<220> FEATURE:
<223> OTHER INFORMATION: synthetic sequence

<400> SEQUENCE: 18
gttagggtta gacaa                                                    15

<210> SEQ ID NO 19
<211> LENGTH: 9
<212> TYPE: DNA
<213> ORGANISM: Artificial sequence
<220> FEATURE:
<223> OTHER INFORMATION: synthetic sequence

<400> SEQUENCE: 19 gggttagac                                                            9

<210> SEQ ID NO 20
<211> LENGTH: 9
<212> TYPE: DNA
<213> ORGANISM: Artificial sequence
<220> FEATURE:
<223> OTHER INFORMATION: synthetic sequence

<400> SEQUENCE: 20 cagttaggg                                                            9

<210> SEQ ID NO 21
<211> LENGTH: 12
<212> TYPE: DNA
<213> ORGANISM: Artificial sequence
<220> FEATURE:
<223> OTHER INFORMATION: synthetic sequence

<400> SEQUENCE: 21
cccttctcag tt                                                       12

<210> SEQ ID NO 22
<211> LENGTH: 12
<212> TYPE: DNA
<213> ORGANISM: Artificial sequence
<220> FEATURE:
<223> OTHER INFORMATION: synthetic sequence

<400> SEQUENCE: 22
cgcccttctc ag                                                       12

```
<210> SEQ ID NO 23
<211> LENGTH: 11
<212> TYPE: RNA
<213> ORGANISM: Artificial sequence
<220> FEATURE:
<223> OTHER INFORMATION: synthetic sequence

<400> SEQUENCE: 23
cuaacccuaa c                                                          11

<210> SEQ ID NO 24
<211> LENGTH: 13
<212> TYPE: DNA
<213> ORGANISM: Artificial sequence
<220> FEATURE:
<223> OTHER INFORMATION: synthetic sequence

<400> SEQUENCE: 24
taggtgtaag caa                                                        13
```